US011648157B2

(12) United States Patent
Fukasawa et al.

(10) Patent No.: US 11,648,157 B2
(45) Date of Patent: *May 16, 2023

(54) ABSORBENT ARTICLE AND METHOD FOR MANUFACTURING PULL-ON ABSORBENT ARTICLE INCLUDING LEG-CIRCUMFERENCE EXTENSION SECTIONS

(71) Applicant: UNICHARM CORPORATION, Ehime (JP)

(72) Inventors: Jun Fukasawa, Kagawa (JP); Toshiyasu Yoshioka, Kagawa (JP); Kunihiko Katsuragawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 1020 days.

This patent is subject to a terminal disclaimer.

(21) Appl. No.: 16/326,918

(22) PCT Filed: Jul. 5, 2017

(86) PCT No.: PCT/JP2017/024696
§ 371 (c)(1),
(2) Date: Feb. 21, 2019

(87) PCT Pub. No.: WO2018/042875
PCT Pub. Date: Mar. 8, 2018

(65) Prior Publication Data
US 2019/0209397 A1   Jul. 11, 2019

(30) Foreign Application Priority Data

Aug. 29, 2016  (JP) .............................. JP2016-167106
Aug. 29, 2016  (JP) .............................. JP2016-167107

(51) Int. Cl.
*A61F 13/49* (2006.01)
*A61F 13/494* (2006.01)
(Continued)

(52) U.S. Cl.
CPC .. *A61F 13/49019* (2013.01); *A61F 13/15585* (2013.01); *A61F 13/15739* (2013.01);
(Continued)

(58) Field of Classification Search
CPC ............ A61F 13/49406; A61F 13/4963; A61F 13/49; A61F 13/494; A61F 2013/15861;
(Continued)

(56) References Cited

U.S. PATENT DOCUMENTS 6,123,694 A * 9/2000 Pieniak ............... A61F 13/4942
604/385.01
8,043,275 B2 * 10/2011 Peterson ............. A61F 13/4942
604/385.27
(Continued)

FOREIGN PATENT DOCUMENTS

AU  2010287902  *  3/2011
CN  101239016 A  8/2008
(Continued)

OTHER PUBLICATIONS

International Preliminary Report on Patentability in PCT Application No. PCT/JP2017/024696, dated Sep. 19, 2017, 17pp.
(Continued)

*Primary Examiner* — Michele M Kidwell
(74) *Attorney, Agent, or Firm* — Hauptman Ham, LLP

(57) ABSTRACT

An absorbent article including an absorbent main body including an absorbent body. The absorbent main body having a longitudinal direction conforming to a vertical direction; and waist-circumference sections in a pair respectively located on one end side and another end side in the
(Continued)

longitudinal direction of the absorbent main body. The waist-circumference sections each including an elastic memberstretchable in a lateral direction. The absorbent main body including a pair of extension sections respectively extending outward on two sides of the absorbent body. The extension sections each having an elastic member stretchable in the vertical direction. The extension sections are formed extending laterally outward from a position on a non-skin side of the absorbent body using a continuous sheet that is continuous in the lateral direction. A welded region having a predetermined length in the lateral direction is in a portion where each of the extension sections forms a leg opening.

9 Claims, 16 Drawing Sheets

(51) Int. Cl.
  *A61F 13/15* (2006.01)
  *A61F 13/496* (2006.01)
(52) U.S. Cl.
  CPC ...... *A61F 13/15804* (2013.01); *A61F 13/494* (2013.01); *A61F 13/496* (2013.01); *A61F 13/49061* (2013.01); *A61F 13/4963* (2013.01); *A61F 13/49413* (2013.01); *A61F 2013/49093* (2013.01)
(58) Field of Classification Search
  CPC .......... A61F 13/49019; A61F 13/49061; A61F 2013/49093; A61F 2013/15878
  See application file for complete search history.

(56) References Cited

U.S. PATENT DOCUMENTS

| | | | | |
|---|---|---|---|---|
| 10,925,778 | B2* | 2/2021 | Mukai | A61F 13/4942 |
| 11,337,868 | B2* | 5/2022 | Fukasawa | A61F 13/49466 |
| 2003/0171731 | A1* | 9/2003 | Johnston | A61F 13/4942 |
| | | | | 604/385.27 |
| 2005/0131375 | A1* | 6/2005 | Sasaki | A61F 13/496 |
| | | | | 604/385.28 |
| 2010/0100069 | A1* | 4/2010 | Nakaoka | A61F 13/4753 |
| | | | | 604/385.101 |
| 2012/0035573 | A1 | 2/2012 | Kuwano et al. | |
| 2012/0277703 | A1* | 11/2012 | Rhein | A61F 13/49007 |
| | | | | 604/367 |
| 2013/0255865 | A1* | 10/2013 | Brown | A61F 13/15804 |
| | | | | 156/161 |
| 2014/0005621 | A1 | 1/2014 | Roe et al. | |
| 2016/0278996 | A1* | 9/2016 | Takahashi | A61F 13/4942 |
| 2017/0239104 | A1* | 8/2017 | Jang | A61F 13/495 |
| 2017/0333262 | A1* | 11/2017 | Chatterjee | A61F 13/49473 |
| 2019/0192357 | A1* | 6/2019 | Fukasawa | A61F 13/494 |
| 2019/0254884 | A1* | 8/2019 | Mukai | A61F 13/4942 |
| 2019/0254886 | A1* | 8/2019 | Köktürk et al. | A61F 13/49413 |

FOREIGN PATENT DOCUMENTS

| | | |
|---|---|---|
| CN | 101803976 A | 8/2010 |
| JP | 2005-514244 A | 5/2005 |
| JP | 2012-192058 A | 10/2012 |
| JP | 2013-13580 A | 1/2013 |
| JP | 2013-13682 A | 1/2013 |
| JP | 2013-70711 A | 4/2013 |
| JP | 2014-171688 A | 9/2014 |

OTHER PUBLICATIONS

Office Action in EA Application No. 201990601/31, dated Jun. 2, 2020, 4pp.
Extended European Search Report in EP Application No. 17845885.7, dated Jun. 4, 2019, 7pp.
Office Action in JP Application No. 2016-167106, dated Apr. 28, 2020, 9pp.
Office Action in CN Application No. 201780052189.0, dated Aug. 10, 2021, 18pp.
Office Action in IN Application No. 201927003179, dated Jun. 22, 2021, 6pp.
Office Action in BR Application No. BR112019002317-8, dated Dec. 10, 2021, 7pp.
International Search Report in PCT Application No. PCT/JP2017/024696, dated Sep. 19, 2017, 4pp.
Office Action in CN Application No. 201780052189.0, dated Jan. 26, 2021, 11pp.
Office Action in IND application No. 201927003179, dated Mar. 24, 2023, 2pp.

* cited by examiner

ABSORBENT ARTICLE AND METHOD FOR MANUFACTURING PULL-ON ABSORBENT ARTICLE INCLUDING LEG-CIRCUMFERENCE EXTENSION SECTIONS

RELATED APPLICATIONS

The present application is a National Phase of PCT/JP2017/024696, filed Jul. 5, 2017, and claims priority based on Japanese Patent Application No. 2016-167106, filed Aug. 29, 2016, and Japanese Patent Application No. 2016-167107, filed Aug. 29, 2016.

TECHNICAL FIELD

The present disclosure relates to an absorbent article and a method for manufacturing a pull-on absorbent article.

BACKGROUND ART

An absorbent article includes a disposable diaper as an example thereof. A disposable diaper including an absorbent main body and a waist belt is disclosed in Patent Literature 1. The waist belt of this diaper includes an inner sheet portion, an outer sheet portion, and a cushion forming sheet portion placed between these sheet portions. A waist stretchable member is also fixed in a stretched state between the outer sheet portion and the cushion forming sheet portion. The cushion forming sheet portion and the inner sheet portion are joined together in a discontinuous manner along the waist circumference. Accordingly, gaps are formed in non-joined portions where the cushion forming sheet portion and the inner sheet portion are not joined together, thereby being able to reduce irritation caused to a wearer's skin.

CITATION LIST

Patent Literature

[PTL 1] Japanese Patent Application Publication No. 2013-70711

SUMMARY OF INVENTION

Technical Problem

In order to prevent lateral leakage of excrement, the above diaper is configured such that second barrier cuffs (extension sections) provided so as to extend outward on both lateral sides of an absorbent body, thereby closely fitting the second barrier cuffs around the wearer's legs. Each of the second barrier cuffs includes three stretchable members placed in rows along the lateral direction, and has a width in the lateral direction. The second barrier cuffs are, however, easily affected by the waist stretchable members, and thus might contract in the lateral direction or curl. In such a case, the second barrier cuffs are not be able to closely fit around the wearer's legs through face contact, thereby reducing effectiveness in prevention of lateral leakage. Further, the second barrier cuffs are formed by joining a side sheet and a cover sheet together. Accordingly, excrement is likely to seep out from a seam between the two sheets.

The present disclosure achieved in consideration of such issues as describe above, an object of the present disclosure is to provide an absorbent article that is suppressed from leaking from around the legs.

Solution to Problem

A primary aspect of the present disclosure is an absorbent article having a vertical direction and a lateral direction, the absorbent article comprising: an absorbent main body including an absorbent body, the absorbent main body having a longitudinal direction that conforms to the vertical direction; and waist-circumference sections in a pair respectively located on one end side and another end side in the longitudinal direction of the absorbent main body, the waist-circumference sections including an elastic member stretchable in the lateral direction, the absorbent main body including extension sections in a pair respectively extending outward on two lateral sides of the absorbent body, the extension sections each having an elastic member stretchable in the vertical direction placed therein, the extension sections being formed extending laterally outward from a position on a non-skin side of the absorbent body using a continuous sheet that is continuous in the lateral direction, a welded region having a predetermined length in the lateral direction being placed in a portion where each of the extension sections forms a leg opening.

At least following matters will become clear from the descriptions of the present specification with reference to the accompanying drawings.

Advantageous Effects of Invention

According to the present disclosure, it is possible to provide a pull-on absorbent article that is suppressed from leaking from around legs.

DESCRIPTION OF EMBODIMENTS

Figure 1:
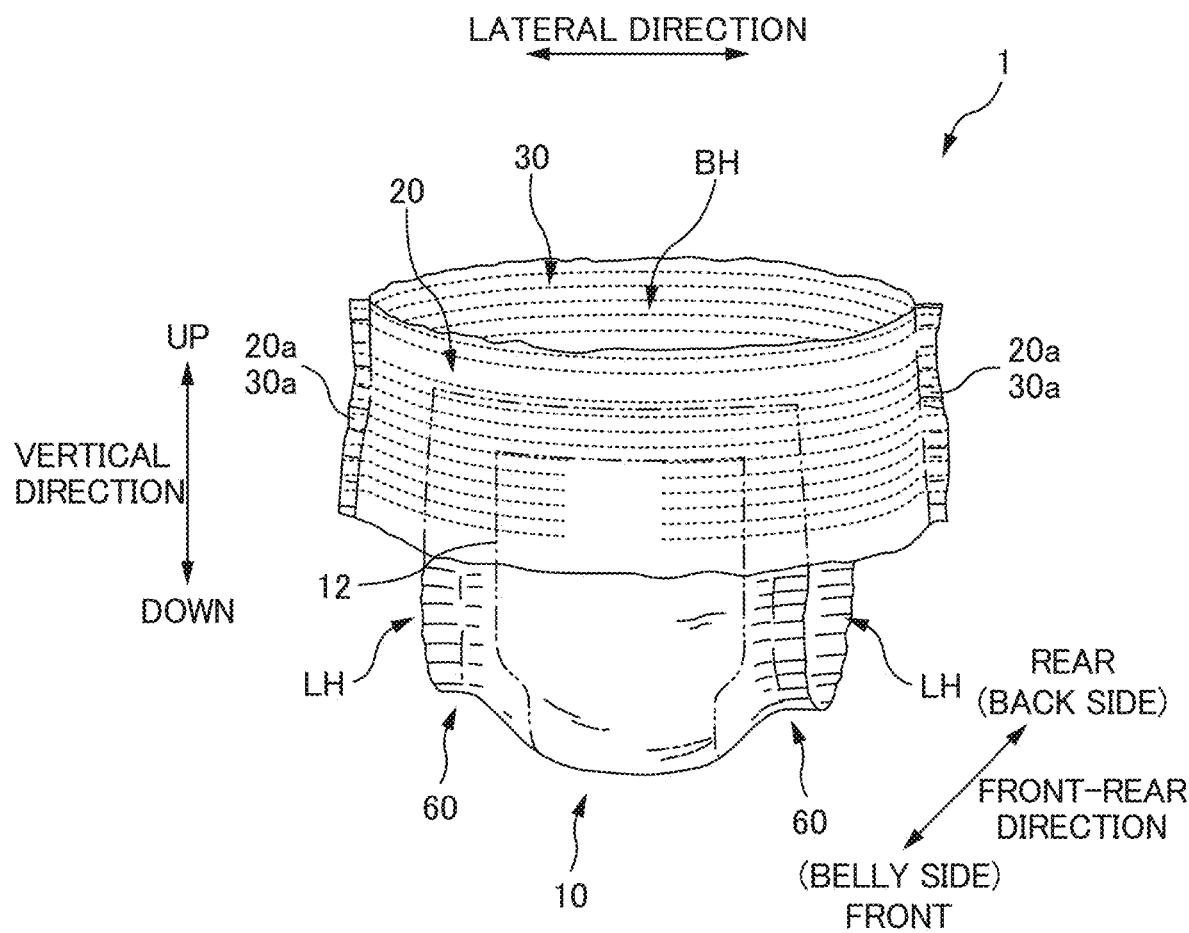
FIG. 1 is a schematic perspective view of a pull-on disposable diaper 1.

At least following matters will become clear from the descriptions of the present specification with reference to the accompanying drawings.

An absorbent article having a vertical direction and a lateral direction, the absorbent article comprising: an absorbent main body including an absorbent body, the absorbent main body having a longitudinal direction that conforms to the vertical direction; and waist-circumference sections in a pair respectively located on one end side and another end side in the longitudinal direction of the absorbent main body, the waist-circumference sections including an elastic member stretchable in the lateral direction, the absorbent main body including extension sections in a pair respectively extending outward on two lateral sides of the absorbent body, the extension sections each having an elastic member stretchable in the vertical direction placed therein, the extension sections being formed extending laterally outward from a position on a non-skin side of the absorbent body using a continuous sheet that is continuous in the lateral direction, a welded region having a predetermined length in the lateral direction being placed in a portion where each of the extension sections forms a leg opening.

According to such an absorbent article, the extension sections have higher stiffness in the lateral direction at the portions where the extension sections form the leg openings, and such portions are likely to be maintained with some widths in the lateral direction, thereby being able to closely fit around the legs of the wearer through face contact. Accordingly, leakage from around the legs is suppressed. Further, there is no seam in a sheet exposed to the non-skin side faces of the extension sections and the vicinity thereof, thereby suppressing seeping out of excrement from seams between sheets.

In such an absorbent article, the welded region includes a first welded region and a second welded region, and in the portion where each of the extension sections forms the leg opening, a portion of the continuous sheet where the first welded region is placed and a portion of the continuous sheet where the second welded region is placed are superimposed on each other by being folded in a thickness direction of the extension sections.

According to such an absorbent article, the stiffness in the lateral direction is further increased in the portions where the extension sections form the leg openings, and thus such portions are likely to be maintained with some widths in the lateral direction, thereby reliably suppressing leakage from around the legs.

In such an absorbent article, at least a portion of the first welded regions and at least a portion of the second welded regions are not superimposed on each other in plan view in the thickness direction.

According to such an absorbent article, the welded regions are present in a wider flat surface range in the portions where the extension sections form the leg openings, so that the stiffness in the lateral direction is further increased, thereby more reliably suppressing leakage from around the legs.

In such an absorbent article, the welded region is placed inside of an outer end in the lateral direction of each of the extension sections.

According to such an absorbent article, laterally outer end portions of the portions where the extension sections form the leg openings are soft, and are accordingly comfortable to the skin. Further, the sandwiching force of the wearer's legs is absorbed, and thus such portions are likely to be maintained with some widths in the lateral direction, thereby suppressing leakage from around the legs.

In such an absorbent article, the continuous sheet is folded on itself in the portion where each of the extension sections forms the leg opening, a liquid impermeable sheet is placed between the absorbent body and the continuous sheet and between portions of the folded continuous sheet, and the liquid impermeable sheet is placed inside of the outer end in the lateral direction of each of the extension sections.

According to such an absorbent article, laterally outer end portions of the portions where the extension sections form the leg openings are soft, and are accordingly comfortable to the skin. Further, the sandwiching force of the wearer's legs is absorbed, and thus such portions are likely to be maintained with some widths in the lateral direction, thereby suppressing leakage from around the legs.

In such an absorbent article, the elastic member that is stretchable in the vertical direction and placed in each of the extension sections intersects with the welded region.

According to such an absorbent article, in the portions where the extension sections form the leg openings, the portions where the welded regions are placed are integrally raised toward the wearer's side by virtue of the contraction of the elastic members, thereby closely fitting around the legs of the wearer through face contact.

In such an absorbent article, the elastic member that is stretchable in the vertical direction and placed in each of the extension sections is placed at a position between the absorbent body and the welded region in the lateral direction.

According to such an absorbent article, the portions where the extension sections form the leg openings are raised toward the wearer's side by virtue of the contraction of the elastic members, so that an upright height is ensured, thereby being able to closely fit around the legs of the wearer.

In such an absorbent article, the elastic member that is stretchable in the vertical direction and placed in the extension section is placed at a position of the outer end in the lateral direction of each of the extension sections.

According to such an absorbent article, the positions where the extension sections form the leg openings are able to closely fit the wearer up to the positions corresponding to the outer ends in the lateral direction.

In such an absorbent article, the absorbent main body includes leak prevention wall sections in a pair in two lateral side portions of the absorbent body, respectively, the leak prevention wall sections being raisable toward a wearer, and the leak prevention wall sections are formed using the continuous sheet.

According to such an absorbent article, there are no seam in sheet at the boundary between the extension section and the leak prevention wall section, thereby further suppressing leakage from around the legs.

In such an absorbent article, the extension sections in a pair are formed using the continuous sheet that is shared between the extension sections.

According to such an absorbent article, there is no seam in a sheet exposed to the non-skin side face of the absorbent main body, thereby suppressing leakage from a seam between sheets. Further, the pair of extension sections are integrally raised together when the diaper is worn, and thus the pair of extension sections can closely fit around the legs of the wearer in a balanced manner.

Further, a method for manufacturing a pull-on absorbent article having a vertical direction, a lateral direction, and a thickness direction, the pull-on absorbent article including an absorbent body and an exterior sheet, the absorbent body having a longitudinal direction conforming to the vertical direction, the exterior sheet being superimposed on the absorbent body on a non-skin side, the exterior sheet extending laterally outward from a position on a non-skin side of the absorbent body, the exterior sheet being continuous in the lateral direction, the method comprising: a welded region forming step of forming a welded region having a predetermined length in the lateral direction by welding a portion where the exterior sheet is superimposed on itself in the thickness direction; an elastic member placing step of placing an elastic member in a predetermined region of the exterior sheet, the elastic member being stretchable in the vertical direction; and a leg-circumference extension section forming step of forming leg-circumference extension sections each in which at least a portion of the elastic member overlaps in the lateral direction with the welded region, the leg-circumference extension sections respectively extending on two lateral sides of the absorbent body.

According to such a method for manufacturing a pull-on absorbent article, the leg-circumference extension sections are suppressed from contracting and curling in the lateral direction, by virtue of the provision of the welded regions. This makes it possible to provide a pull-on absorbent article in which the leg-circumference extension sections are likely to be maintained in a planar shape with some widths in the lateral direction. Moreover, a contraction force in the vertical direction caused by the leg-circumference elastic members acts, thereby forming many creases along the lateral direction on the surface of the leg-circumference extension sections. With the undulations of such creases, it is possible to provide a pull-on absorbent article having pleasant feel to the touch.

In such a method for manufacturing a pull-on absorbent article, it is preferable that, in the welded region forming step, two end portions in the lateral direction of the exterior sheet in an unfolded state are folded back on themselves in the lateral direction from outside to inside, and the welded region is formed in a folded portion obtained by folding the exterior sheet in the thickness direction, and in the leg-circumference extension section forming step, the leg-circumference extension section is formed by folding two end portions of the exterior sheet in the lateral direction on themselves once again from outside to inside.

According to such an absorbent article, the extension sections are integrally formed by folding a single exterior sheet back on itself, and thus there is no seam in a sheet member formed in the extension sections. This makes it possible to suppress leakage of excrement from a seam between sheets in the vicinity around the legs of the wearer.

In such a method for manufacturing a pull-on absorbent article, it is preferable that, in the elastic member placing step, the elastic member is placed so as to overlap with at least a portion of the welded regions in the lateral direction.

According to such a method for manufacturing a pull-on absorbent article, welding can be performed without cutting leg-circumference elastic members. That is, in the leg-circumference extension sections, the welded regions can be formed in regions overlapping the leg-circumference elastic members without damaging the stretching force of the leg-circumference elastic members. Accordingly it is possible to easily manufacture a pull-on absorbent article having leg-circumference extension sections that are likely to be maintained in a planar shape and less likely to be curled when worn.

In such a method for manufacturing a pull-on absorbent article, it is preferable that the welded region includes a first welded region and a second welded region, and the first welded region and the second welded region are discontinuous in the lateral direction.

According to such a method for manufacturing a pull-on absorbent article, it is possible to provide portions having high stiffness and portions having low stiffness, in the portions where the welded regions are formed and the portions where the welded regions are not formed, in the lateral direction in the exterior sheet.

In such a method for manufacturing a pull-on absorbent article, it is preferable that, in the leg-circumference extension section forming step, the exterior sheet is folded back on itself at a predetermined position between the first welded region and the second welded region in the lateral direction.

According to such a method for manufacturing a pull-on absorbent article, the stiffness of the exterior sheet does not become too high at predetermined positions, thereby being able to tightly folding back the exterior sheet at these predetermined positions. Accordingly, the leg-circumference extension sections are likely to be formed into neat planar shapes.

In such a method for manufacturing a pull-on absorbent article, it is preferable that the welded region is formed to be inclined at a predetermined angle with respect to the lateral direction.

According to such a method for manufacturing a pull-on absorbent article, the welded regions are formed while the point to which pressure is applied is being sequentially shifted along with the rotation of the embossing roller that is configured to form the welded region, so that local welding defects or the like are less likely to occur and stable welding is achieved. Moreover, since the place where pressure is applied is sequentially shifted, the projections (e.g., ultrasound horns) provided on the outer circumferential face of the embossing roller are less likely to be worn out, thereby being able to efficiently manufacture a pull-on absorbent article.

In such a method for manufacturing a pull-on absorbent article, it is preferable that the welded region is formed such that a plurality of dots are arranged in the lateral direction.

According to such a method for manufacturing a pull-on absorbent article, partial welding is performed by using the dot-shaped weld portions, so that the shape of each of the weld portions (dots) becomes small, thereby easily concentrating and repeatedly applying ultrasonic vibrations or the like onto individual points. This makes it possible to stably perform welding over the entire welded region.

In such a method for manufacturing a pull-on absorbent article, it is preferable that leak prevention wall sections in a pair configured to be raised toward a wearer's skin side are respectively formed in two lateral side portions of the absorbent body, and the welded region is formed at a position not overlapping in the lateral direction with a position corresponding to a base for raising each of the leak prevention wall sections.

According to such a method for manufacturing a pull-on absorbent article, the portion (the side joined portions 53) serving as the base for raising each of the leak prevention wall sections does not overlap with the welded region, thereby suppressing increase in the stiffness of the exterior sheet at this base. Accordingly, the exterior sheet is likely to be folded naturally based on the positions of the side joined portions, thereby being able to raise the leak prevention wall sections easily.

In such a method for manufacturing a pull-on absorbent article, it is preferable that a plurality of the elastic members are provided side by side in the lateral direction in each of the leg-circumference extension sections, and the elastic member provided on an innermost side in the lateral direction among the plurality of elastic members is placed between the absorbent body and the welded region in the lateral direction.

According to such a method for manufacturing a pull-on absorbent article, the portions outside in the lateral direction of the elastic members (61a) in the leg-circumference extension sections serve as the bases for being raised toward the wearer's skin side when the pull-on absorbent article is worn, by virtue of the contraction of the elastic member (61a) provided innermost in the lateral direction, and the upright height of the leg-circumference extension sections is ensured. Accordingly, the leg-circumference extension sections are likely to closely fit around the legs of the wearer.

In such a method for manufacturing a pull-on absorbent article, it is preferable that the plurality of elastic members are provided side by side in the lateral direction in each of the leg-circumference extension sections, and the elastic member provided on an outermost side in the lateral direction among the plurality of elastic members is placed at an outer end in the lateral direction of each of the leg-circumference extension sections.

According to such a method for manufacturing a pull-on absorbent article, the leg-circumference extension sections are likely to closely fit around the legs of the wearer by virtue of the contraction force of the elastic members (61d) provided on the outermost side in the lateral direction. Accordingly, the degradation in fit of the leg-circumference extension sections are likely to be suppressed, even in a case where the leg-circumference extension sections are less likely to be maintained in a flat plane shape in the laterally outer end portions.

In such a method for manufacturing a pull-on absorbent article, a liquid impermeable back sheet is provided on a skin side of the elastic member that is placed so as to overlap with the welded region in the lateral direction.

According to such a method for manufacturing a pull-on absorbent article, the back sheet is placed so as to cover the skin side of the leg-circumference elastic members, thereby suppressing the leg-circumference elastic members from being exposed to the skin side, so that the adhesive applied to the surfaces of the leg-circumference elastic members is suppressed from adhering to the body of the wearer. Moreover, since the end joined portions and the side joined portions are suppressed from contacting the leg-circumference elastic members, a contraction force caused by the leg-circumference elastic members is suppressed from acting on the waist-circumference sections.

EMBODIMENTS

An absorbent article (a pull-on absorbent article) according to the present disclosure will now be described using the following embodiment in which a "pull-on disposable diaper" is employed as an example thereof. The pull-on disposable diaper according to an embodiment of the present disclosure may be used for infants or adults.

Basic Configuration of Pull-On Disposable Diaper

Figure 2:
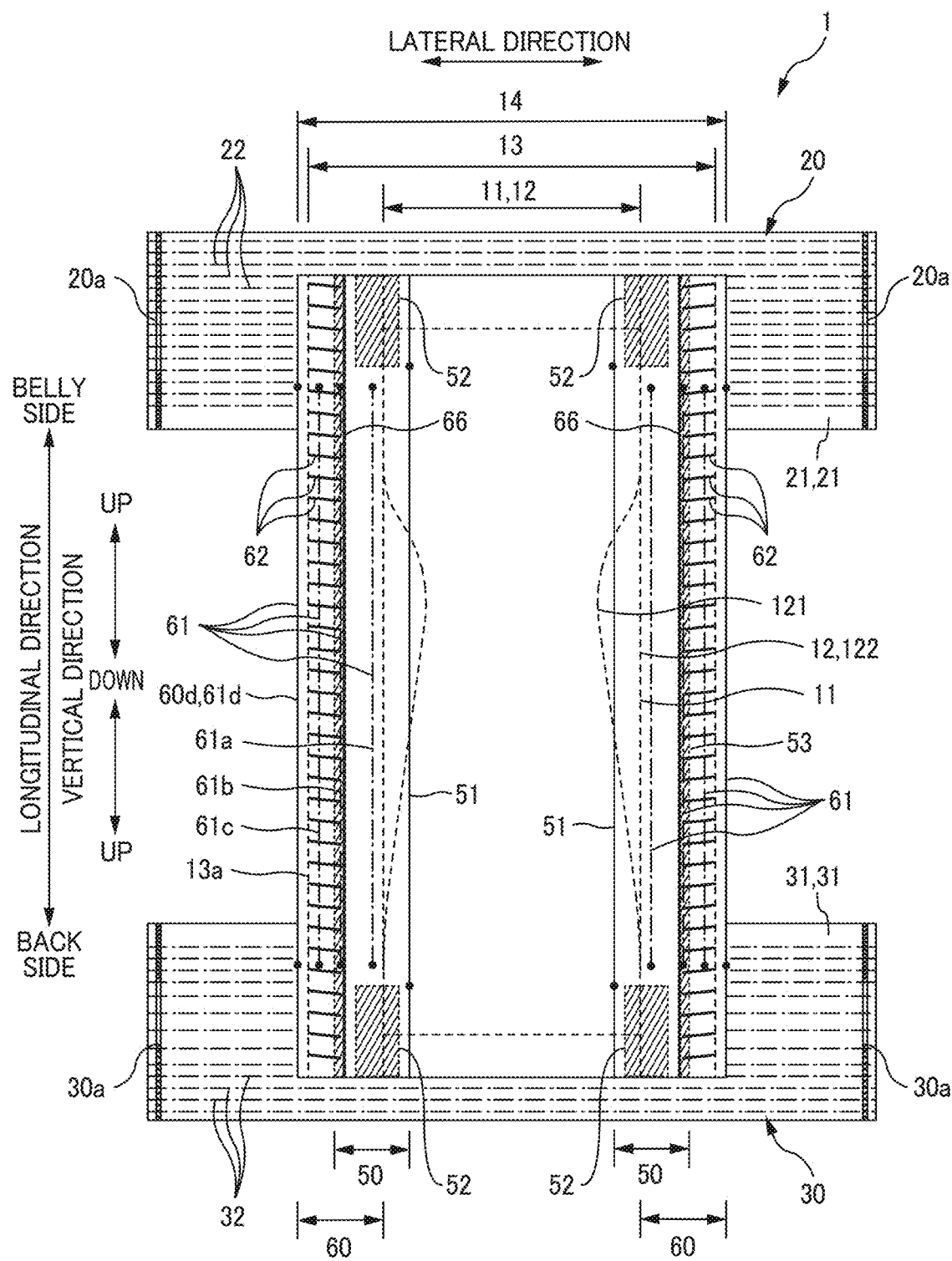
FIG. 2 is a schematic plan view of the diaper 1 in an unfolded and extended state when viewed from a skin-side.
Figure 3:
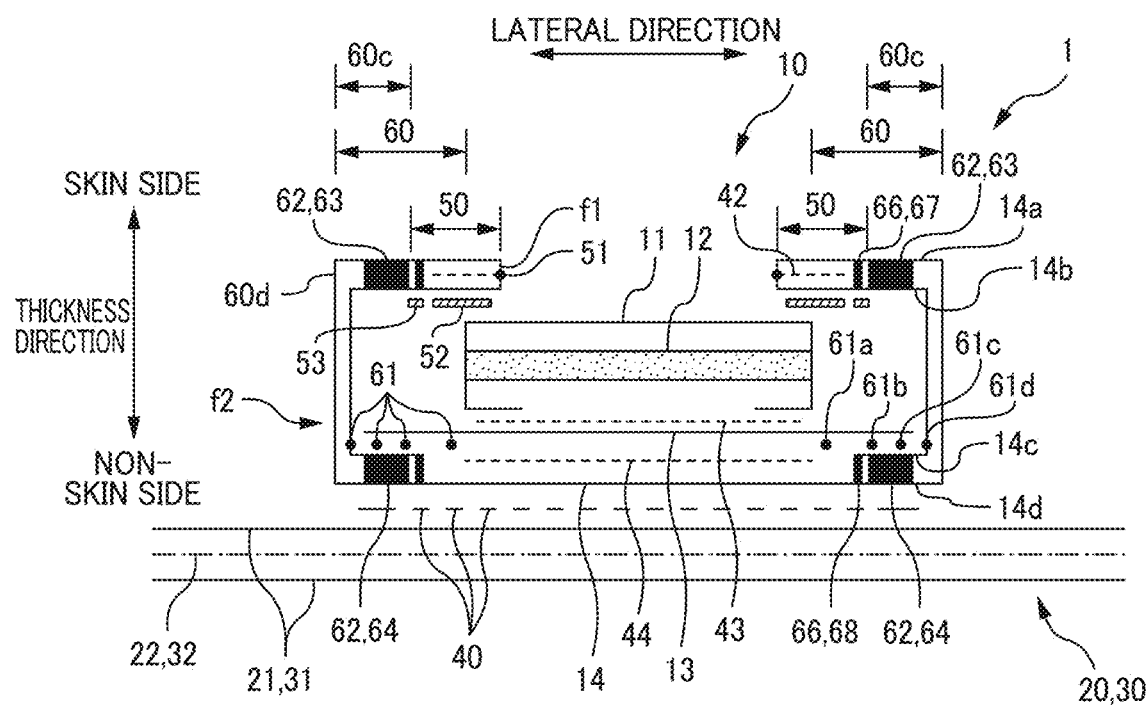
FIG. 3 is a schematic cross-section of the diaper 1.
Figure 4A:
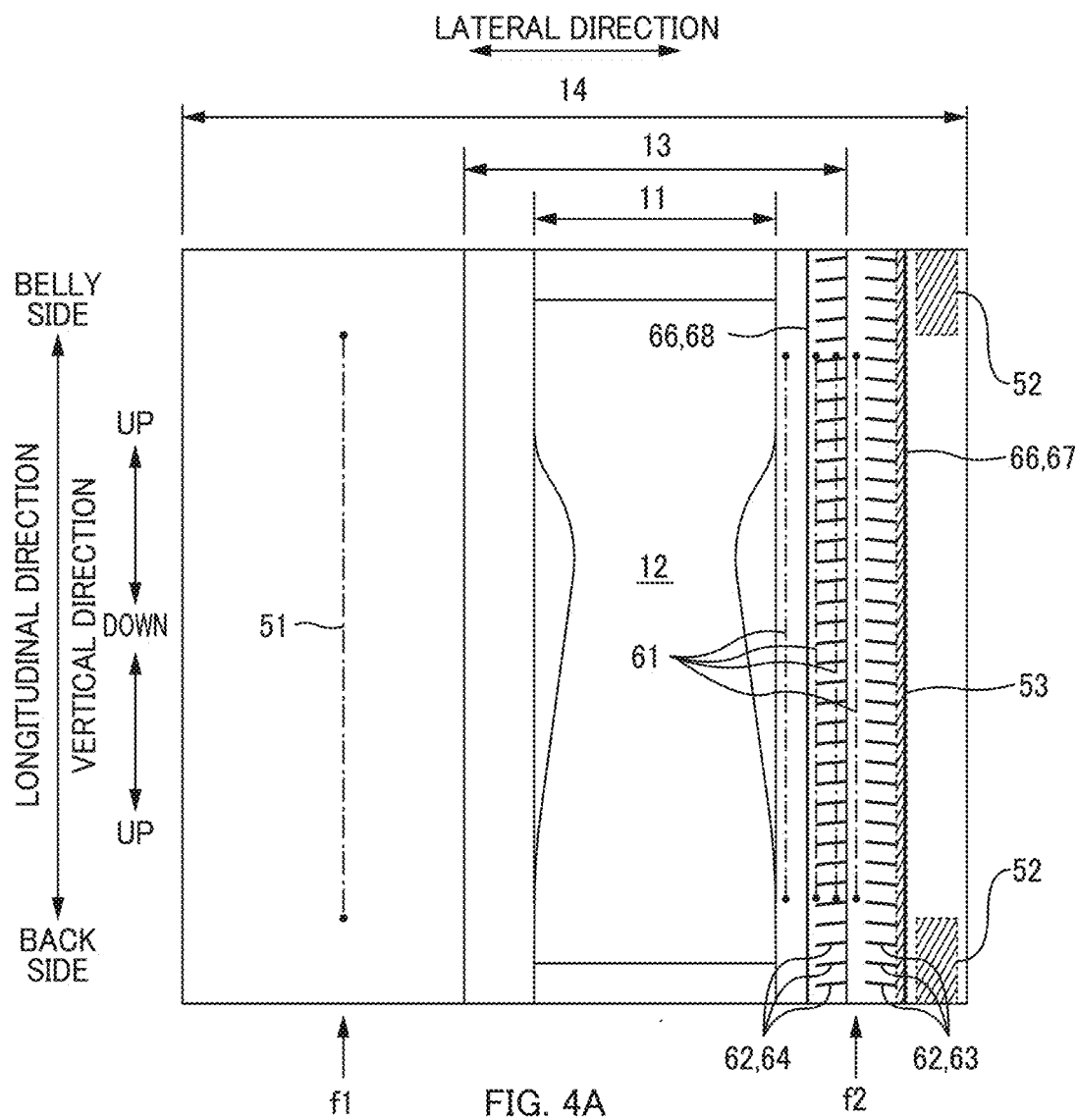
FIG. 4A and FIG. 4B are diagrams to explain a method of forming an absorbent main body 10.
Figure 4B:
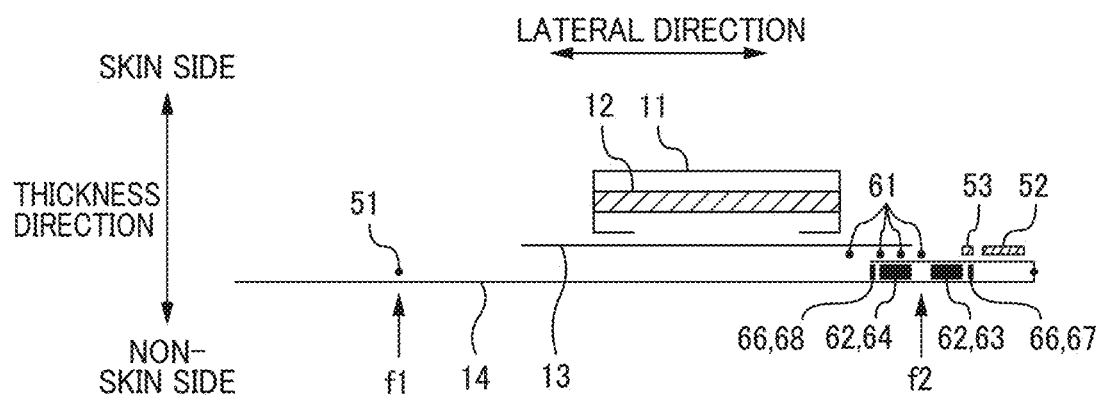
Figure 5:
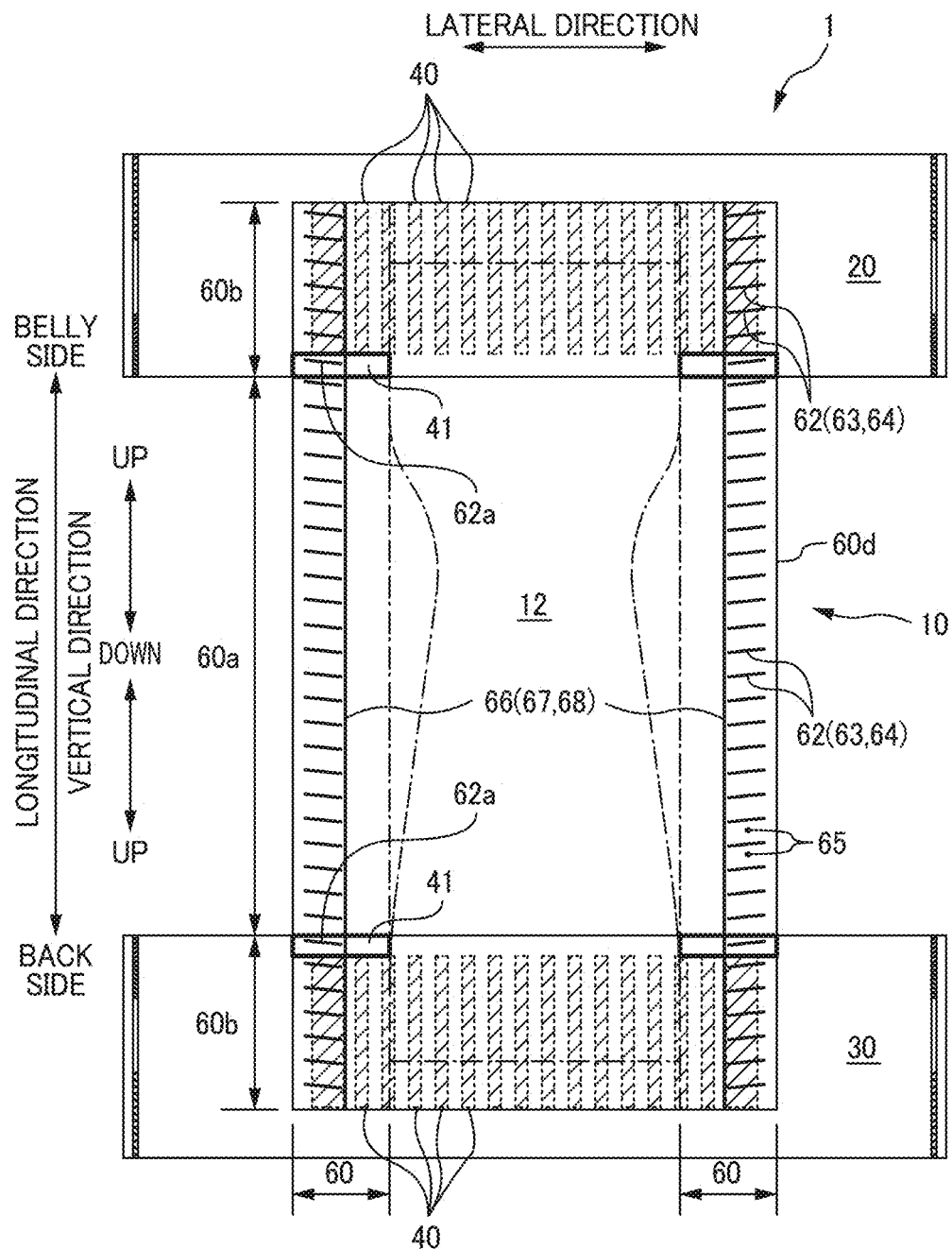
FIG. 5 is an explanatory diagram of the absorbent main body 10 and adhesive regions 40 of a pair of waist-circumference sections 20, 30.

FIG. 1 is a schematic perspective view of a pull-on disposable diaper 1 (hereinafter referred to as a "diaper"). FIG. 2 is a schematic plan view of the diaper 1 in an unfolded and stretched state, as viewed from a skin-side face. FIG. 3 is a schematic cross-section of the diaper 1. FIG. 4A and FIG. 4B are diagrams to explain a method of forming an absorbent main body 10. FIG. 5 is an explanatory diagram of the absorbent main body 10 and adhesive regions 40 of a pair of waist-circumference sections 20, 30. Note that except for FIG. 1, the drawings illustrate states in which the diaper 1 provided with elastic members has been stretched to such an extent that creases in the diaper 1 are not visible. Specifically, the stretched state illustrated indicates a state of being stretched such that the dimensions of members configuring the diaper 1 (such as those of an exterior sheet 14 described later, for example) match or are close to the dimensions of the individual members of their own.

As illustrated in FIG. 1, a vertical direction, a lateral direction, and a front-rear direction are defined in the pull-on diaper 1. A waist opening BH and a pair of leg openings LH are formed in the diaper 1. In the vertical direction, the side of the waist opening BH is an upper side, and the side that will be disposed at the crotch of a wearer is a lower side. In the front-rear direction, the side that will be disposed on the wearer's belly side is a front side, and the side that will be disposed on the wearer's back side is a rear side. The diaper 1 has a thickness direction as illustrated in FIG. 3. The side in the thickness direction that will contact the wearer is a skin side, and the opposite side thereto is the non-skin side.

The diaper 1 is what is referred to as a three-piece type of diaper, and includes an absorbent main body 10 and a pair of waist-circumference sections 20, 30. The absorbent main body 10 has a substantially rectangular shape in plan view, with the longitudinal direction thereof oriented along the vertical direction. The waist-circumference sections 20, 30 have substantially rectangular shapes in plan view, with the longitudinal directions thereof oriented along the lateral direction. The waist-circumference section that will cover a belly region of the wearer out of the pair of waist-circumference sections 20, 30 is also referred to as a front waist-circumference section 20, and the waist-circumference section that will cover a back region of the wearer is also referred to as a back waist-circumference section 30.

As illustrated in the unfolded state in FIG. 2, a central portion of the front waist-circumference section 20 in the lateral direction is positioned on one longitudinal end side of the absorbent main body 10, and a central portion of the back waist-circumference section 30 in the lateral direction is positioned on the other longitudinal end side of the absorbent main body 10. The non-skin-side face of the absorbent main body 10 and the skin-side faces of the pair of waist-circumference sections 20, 30 are then joined together with an adhesive or the like at the adhesive regions 40 illustrated in FIG. 5. From the unfolded state of FIG. 2, the absorbent main body 10 is folded in two by folding the absorbent main body 10 at its substantially central portion in the longitudinal direction such that the front waist-circumference section 20 and the back waist-circumference section 30 are superimposed on each other. Then, by joining two lateral side portions 20a of the front waist-circumference section 20 to two lateral side portions 30a of the back waist-circumference section 30, respectively, the diaper 1 is formed into a pull-on diaper.

The front waist-circumference section 20 and the back waist-circumference section 30 each include two soft sheets (21 and 21, and 31 and 31) of a nonwoven fabric or the like, and a plurality of elastic members 22, 32 such as laterally stretchable elastic strings or the like. In the following description, the elastic members 22, 32 are also referred to as waist-circumference elastic members 22, 32. The plural waist-circumference elastic members 22, 32 are arranged in rows and spaced apart from each other in the vertical direction, and are fixed between the two sheets (21 and 21 or 31 and 31) in a stretched state along the lateral direction. The front waist-circumference section 20 and the back waist-circumference section 30 are accordingly stretchable in the lateral direction, so as to fit the waist of the wearer.

The absorbent main body 10 includes a top sheet 11, an absorbent body 12, a back sheet 13, and the exterior sheet 14, in this order in the thickness direction from the skin side, as illustrated in FIG. 3. The top sheet 11 maybe any sheet as long as it is a liquid permeable sheet, and examples thereof include a hydrophilic air-through nonwoven fabric and a hydrophilic spunbond nonwoven fabric. The back sheet 13 may be any sheet as long as it is a liquid impermeable sheet, and examples thereof include a polyethylene film, a polypropylene film, and the like. The top sheet 11 and the back sheet 13 have sizes that cover the entire absorbent body 12. In an embodiment of the present disclosure, the side portions on the two lateral sides of the top sheet 11 are folded to the non-skin side of the absorbent body 12. The exterior sheet 14 may be a liquid permeable sheet or a liquid impermeable sheet. However, in an embodiment of the present disclosure, since the leak prevention wall sections 50 are formed using the exterior sheet 14, examples of the exterior sheet 14 include a hydrophobic SMS nonwoven fabric and the like.

The absorbent body 12 has a substantially rectangular shape in plan view, and includes an absorbent core 121 for absorbing liquid, and a core-wrapping sheet 122 covering outer peripheral faces of the absorbent core 121. The absorbent core 121 is configured by molding a liquid-absorbent material into a predetermined shape and, in an embodiment of the present disclosure, is molded into a substantially hour-glass shape having a narrowed central portion in the longitudinal direction thereof. Examples of the liquid-absorbent material include materials obtained by containing a highly absorbent polymer (so-called a SAP), etc., in liquid-absorbent fibers, such as pulp fibers. Examples of the core-wrapping sheet 122 include a liquid permeable sheet such as tissue paper, a nonwoven fabric, or the like. Note that the core-wrapping sheet 122 need not be provided.

The absorbent main body 10 includes the pair of leak prevention wall sections 50 and a pair of leg-circumference extension sections 60 (a pair of extension sections). More details are described later, however, in an embodiment of the present disclosure, the pair of leak prevention wall sections 50 and the pair of leg-circumference extension sections 60 are integrally formed such that the two lateral side portions of the single exterior sheet 14 are folded, as illustrated in FIG. 3 and FIG. 4.

The leak prevention wall sections 50 in a pair extend along the longitudinal direction of the absorbent main body 10, and are provided at the two lateral side portions of the absorbent body 12, respectively. More specifically, the leak prevention wall sections 50 are provided so as to span from a position superimposed on the absorbent body 12 to a position extended laterally outward therefrom. The leak prevention wall sections 50 each includes: an elastic member 51 (hereinafter, also referred to as the "LSG elastic member 51") stretchable in the longitudinal direction (the vertical direction of the diaper 1); and a pair of end joined portions 52 and a side joined portion 53 where the exterior sheet 14 for forming the leak prevention wall sections 50 is joined to the top sheet 11 and the back sheet 13. The pairs of end joined portions 52 are respectively placed at the two longitudinal end portions of the absorbent main body 10.

The side joined portions 53 in a pair extend from one end to the other end in the longitudinal direction of the absorbent main body 10, and are placed outside in the lateral direction of the end joined portions 52. Thus, in each of the leak prevention wall sections 50, a portion in the exterior sheet 14 between the pair of end joined portions 52 is raisable toward the wearer (the skin side in the thickness direction) based on the side joined portion 53 by virtue of contraction of the elastic members 51. Accordingly, excrement having laterally flown out is blocked by the leak prevention wall sections 50. However, the diaper 1 may also be configured without the leak prevention wall sections 50.

The leg-circumference extension sections 60 in a pair respectively are parts that extend outwards to the two lateral sides of the absorbent body 12. More specifically, the leg-circumference extension sections 60 are defined as parts from the respective laterally outer ends of the absorbent body 12 to the laterally outer ends of the absorbent main body 10. Moreover, as illustrated in FIG. 5, the leg-circumference extension sections 60 each includes a "leg opening forming portion 60a" to form each of the leg openings LH, and a pair of "overlap portions 60b" that respectively overlap with the front waist-circumference section 20 and the back waist-circumference section 30 in the vertical direction. In other words, the leg-circumference extension sections 60 each include a pair of "overlap portions 60b" respectively superimposed on the front waist-circumference section 20 and the back waist-circumference section 30 in the thickness direction. Each of the leg-circumference extension sections 60 includes four elastic members 61 (hereinafter also referred to as leg-circumference elastic members 61) stretchable in longitudinal direction (the vertical direction of the diaper 1) and placed at an interval in the lateral direction. Accordingly, the leg opening forming portions 60a of the leg-circumference extension sections 60 fit around the legs of the wearer.

A plurality of "lateral welded regions 62 (welded regions of the present disclosure)" are placed in each of the leg-circumference extension sections 60 such that each lateral welded region extends along the lateral direction while being inclined with respect to the lateral direction. The plurality of lateral welded regions 62 include, as illustrated in FIG. 3, a plurality of first lateral welded regions 63 positioned on the skin side in the thickness direction, and a plurality of second lateral welded regions 64 positioned on the non-skin side in the thickness direction. The plurality of first lateral welded regions 63 and the plurality of second lateral welded regions 64 are, as illustrated in FIG. 5, placed at intervals in the longitudinal direction in a row over the entire longitudinal region of each of the leg-circumference extension sections 60.

"Vertical welded regions 66" extending along the vertical direction (longitudinal direction) are respectively placed in the leg-circumference extension sections 60 at positions laterally inside of the lateral welded regions 62. The vertical welded regions 66 are also placed over the entire longitudinal region of each of the leg-circumference extension sections 60, and include first vertical welded regions 67 positioned on the skin side in the thickness direction, and second vertical welded regions 68 positioned on the non-skin side in the thickness direction.

Although an example has been given in which string shaped elastic members such as elastic strings are employed as the elastic members (22, 32, 51, 61) provided in the front waist-circumference section 20, the back waist-circumference section 30, the leak prevention wall sections 50, and the leg-circumference extension sections 60, it is not limited thereto. For example, a single or a plurality of sheet-shaped elastic members such as a stretchable film, a stretchable nonwoven fabric, or the like may be placed therein instead of elastic strings. Moreover, only the parts where stretchability is exhibited in the elastic members (so-called effective length parts) are illustrated in the drawings. Accordingly, parts of the elastic members where stretchability is not exhibited may exist on their longitudinally outer sides of the illustrated elastic members. The placement and numbers of the elastic members are not limited to those of the illustrated configuration.

Method of Forming the Absorbent Main Body 10

A simple description will now be given of a method of forming the pair of leak prevention wall sections 50 and the pair of leg-circumference extension sections 60 using the single exterior sheet 14, with reference to FIGS. 4. The detailed method of manufacturing the absorbent main body 10 in the manufacturing process of the diaper 1 will be explained later.

First, as illustrated on the left side of FIG. 4A and FIG. 4B, the elastic member 51 used for the leak prevention wall section 50 is fixed to each lateral side portion of the exterior sheet 14 in a stretched state along the longitudinal direction. Then, using the lateral position at which the elastic member 51 for each leak prevention wall section 50 is fixed as a fold position f1, the two lateral side portions of the exterior sheet 14 are folded back toward the skin side in the thickness direction (inwards in the lateral direction).

Then, as illustrated on the right side of FIG. 4A and FIG. 4B, the lateral welded regions 62 and the vertical welded regions 66 are formed by partially welding together portions in the exterior sheet 14 having been folded on itself to form a double layer. Specifically, in each of the portions where the exterior sheet 14 is a double layer, the plurality of first lateral welded regions 63 are formed in a portion on the laterally outer side and placed at intervals in the longitudinal direction, and the plurality of second lateral welded regions 64 are formed in a portion on the laterally inner side and placed at intervals in the longitudinal direction. The first vertical welded region 67 is formed laterally outside of the first lateral welded regions 63, and the second vertical welded region 68 is formed laterally inside of the second lateral welded regions 64. The welded regions 62, 66 maybe formed by a known welding method, and examples thereof include heat sealing, ultrasonic welding, welding by laser irradiation, and the like.

An adhesive is then applied to the skin-side face of the double-layered exterior sheet 14 in a portion laterally outside of the lateral welded regions 62, so as to form the end joined portions 52 and the side joined portion 53 of the leak prevention wall sections 50. Then, the four leg-circumference elastic members 61 are fixed to the skin-side face of the exterior sheet 14 at a portion laterally inside of the side joined portion 53 in a stretched state along the longitudinal direction. Thereafter, the back sheet 13 and the absorbent body 12 wrapped in the top sheet 11 are superimposed on and joined to a central portion in the lateral direction of the exterior sheet 14.

Finally, the side portions at the two lateral sides of the exterior sheet 14 are respectively folded back on the skin side in the thickness direction with respect to the top sheet 11 at respective fold positions f2 between the first lateral welded regions 63 and the second lateral welded regions 64, thereby forming the absorbent main body 10 illustrated in FIG. 3. That is, the side portions on the two lateral sides of the exterior sheet 14 each are folded to form a quadruple layer. This results in the first lateral welded regions 63 and the second lateral welded regions 64 being superimposed on each other in the thickness direction and the first vertical welded regions 67 and the second vertical welded regions 68 being superimposed on each other in the thickness direction. In the following description, respective portions of the exterior sheet 14 of a quadruple layer are also referred to as a first sheet portion 14a, a second sheet portion 14b, a third sheet portion 14c, and a fourth sheet portion 14d, in this order from the skin side in the thickness direction. Each leak prevention wall section 50 is constituted by the first sheet portion 14a and second sheet portion 14b, and each leg-circumference extension section 60 is constituted by the first sheet portion 14a to fourth sheet portion 14d.

Leg-Circumference Extension Section 60

Figure 6:
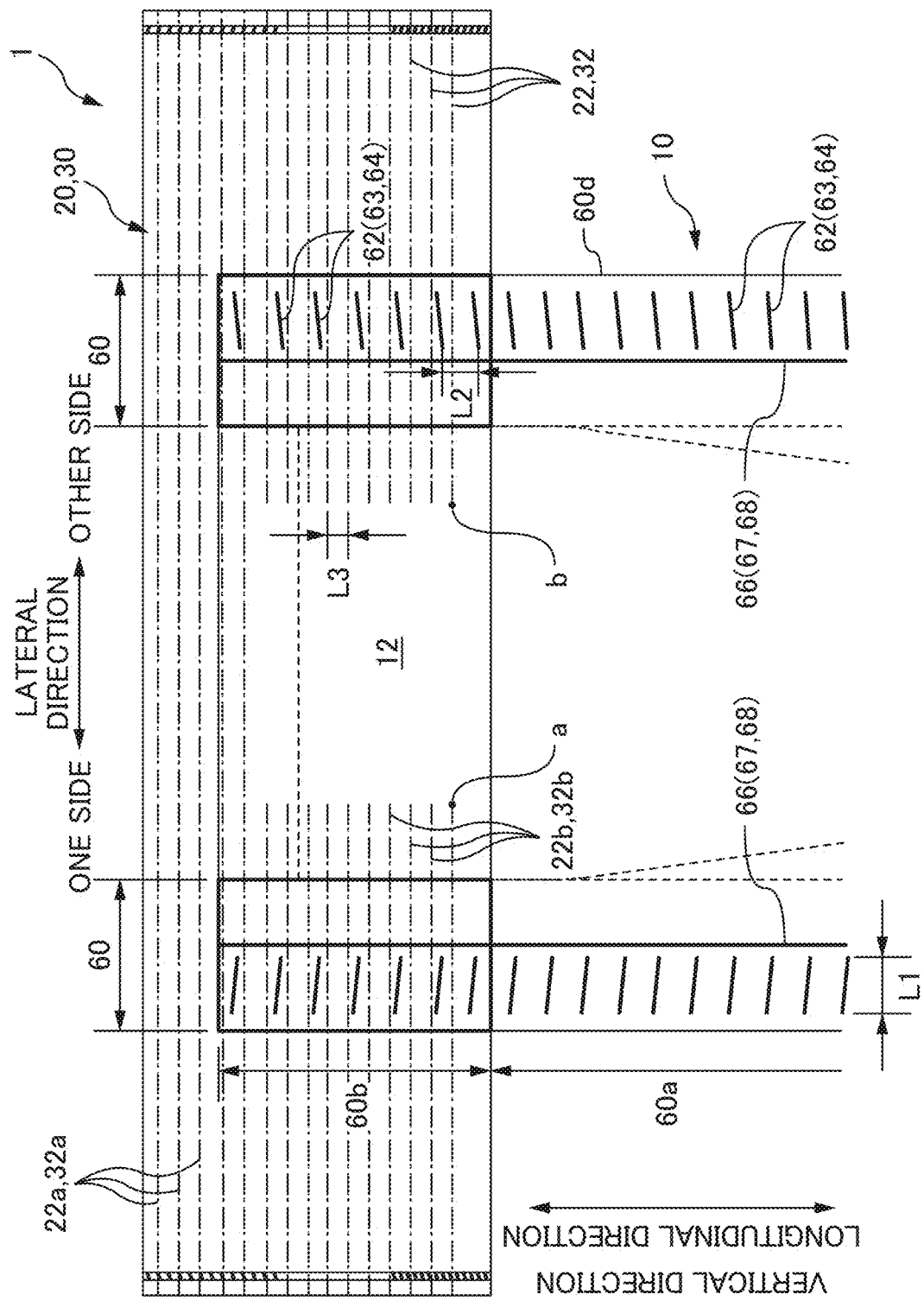
FIG. 6 is a diagram to explain characteristics of leg-circumference extension sections 60.
Figure 7:
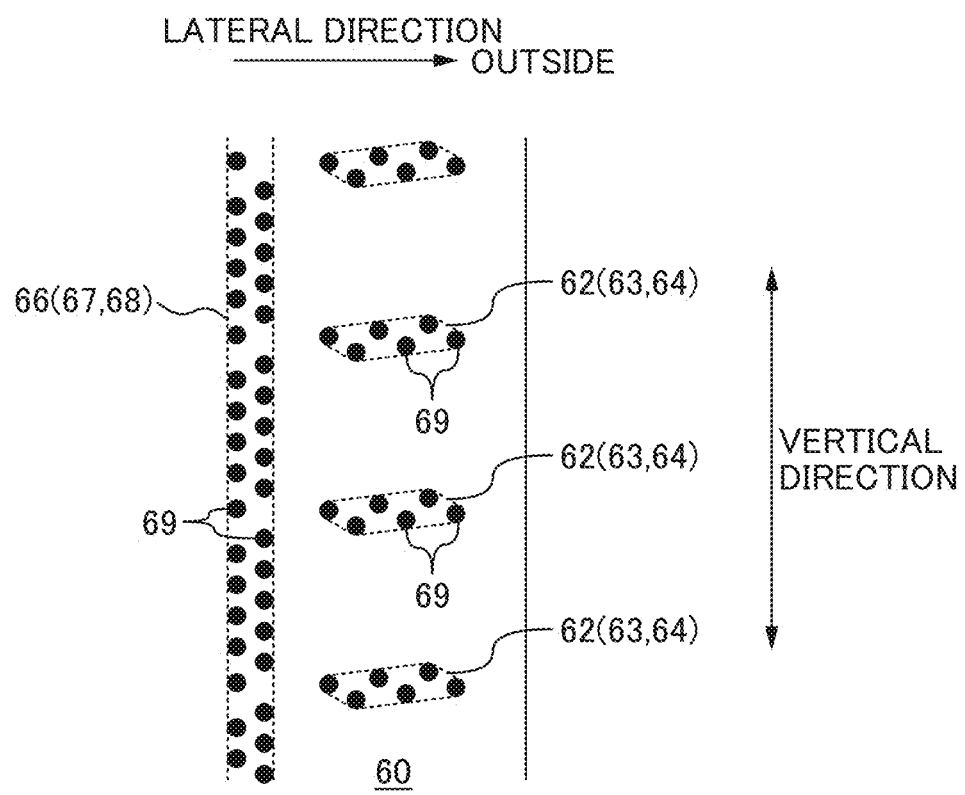
FIG. 7 is an enlarged diagram illustrating lateral welded regions 62 and vertical welded regions 66.
Figure 8:
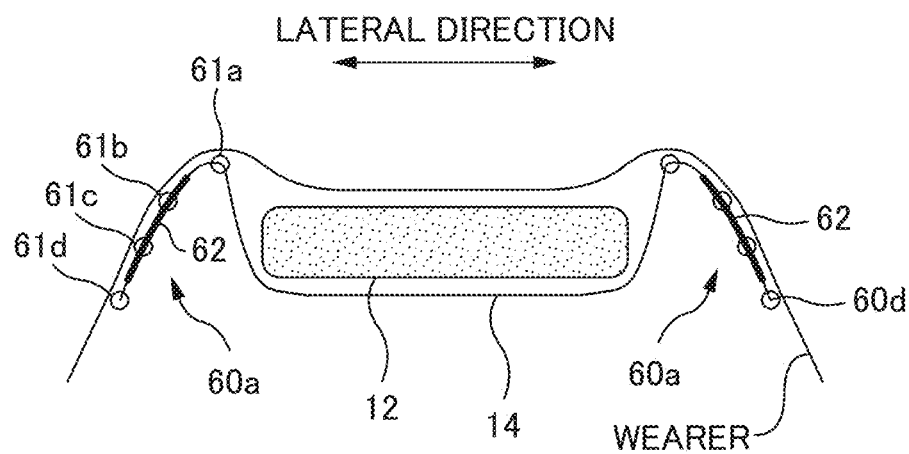
FIG. 8 is a diagram illustrating a state in which the leg-circumference extension sections 60 closely fit the wearer.

FIG. 6 is a diagram for explaining characteristics of the leg-circumference extension sections 60. FIG. 7 is an enlarged diagram illustrating the lateral welded regions 62 and the vertical welded regions 66. FIG. 8 is a diagram illustrating a state in which the leg-circumference extension sections 60 closely fit a wearer. Note that the leak prevention wall sections 50 and the like are omitted in FIG. 8 for the sake of brevity.

In the diaper 1 according to an embodiment of the present disclosure, the lateral width of the leg-circumference extension sections 60 is set to be comparatively wide. For example, in an S size infant diaper 1, when the lateral width of the absorbent main body 10 is 200 mm, the lateral width of each of the leg-circumference extension sections 60 is set at about 40 mm. This makes it possible to closely fit the leg-circumference extension sections 60 around the legs of the wearer through a face having a wide width. Accordingly, excrement is not likely to leak from around the legs. Moreover, since the leg-circumference extension sections 60 are set at the wide lateral width, a plurality of strings (four in this case) of the leg-circumference elastic members 61 can be placed side by side at intervals in the lateral direction. Accordingly, the stretching force of the leg-circumference extension sections 60 that is necessary to stop lateral leakage can be shared among the plurality of the leg-circumference elastic members 61. That is, since the stretching force for each string of the leg-circumference elastic members 61 can be made smaller, a burden on the skin caused by local close contact with the leg-circumference elastic members 61 can be prevented.

The waist-circumference elastic members 22, 32 that are stretchable in the lateral direction are provided in the waist-circumference sections 20, 30 so that the disposable diaper 1 fits around the waist of the wearer. Accordingly, the leg opening forming portions 60a in the leg-circumference extension sections 60 might be affected by the waist-circumference elastic members 22, 32, and contract in the lateral direction or curl inward or outward. For example, if the diapers 1 are individually packaged with the leg opening forming portions 60a in a curled and folded state in the process of manufacturing the diaper 1, traces of folding would remain in the leg opening forming portions 60a, resulting in the diapers 1 being worn with the leg opening forming portions 60a in a folded state.

In particular, the leg-circumference extension sections 60 according to an embodiment of the present disclosure are formed of the exterior sheet 14 of the absorbent main body 10, and include the overlap portions 60b that overlap with the waist-circumference sections 20, 30. As illustrated in FIG. 5, portions of the overlap portions 60b are joined to the waist-circumference sections 20, 30 with the adhesive regions 40. Thus, the overlap portions 60b are likely to be affected by lateral contraction of the waist-circumference sections 20, 30, and accordingly the leg opening forming portions 60a might curl or contract in the lateral direction. This might make it impossible to closely fit the leg-circumference extension sections 60 around the wearer's legs through face contact even though the leg-circumference extension sections 60 are set wide in width.

Further, assuming here that the exterior sheet 14 has about the same lateral width as that of the absorbent body 12, and the leg-circumference extension sections 60 are formed not using the exterior sheet 14 but using side sheets that are members separate from the exterior sheet 14 and that extend laterally outward from the exterior sheet 14, seams between the exterior sheet 14 and the side sheets would be exposed to the non-skin-side face in the vicinity of the leg opening forming portions 60a. Further, assuming that leg opening forming portions 60a are formed not by folding back the two lateral side portions of the exterior sheet 14 to overlap, but by attaching side sheets that are members separate from the exterior sheet 14 onto the skin-side face of the exterior sheet 14, seams between the exterior sheet 14 and the side sheets would be exposed to the laterally outer ends of the leg opening forming portions 60a. With such a configuration, excrement would seep out from the seams between sheets.

In contrast thereto, in the disposable diaper 1 according to an embodiment of the present disclosure, the leg-circumference extension sections 60 are formed using the exterior sheet 14 that is continuous in the lateral direction as well as extends outwards in the lateral direction from a position on the non-skin side of the absorbent body 12. Further, a plurality of the lateral welded regions 62 having a predetermined lateral length (L1 in FIG. 6) are placed in each of the leg opening forming portions 60a ("a portion where each of the extension sections forms a leg portion" corresponding to the present disclosure). Note that the position on the non-skin side of the absorbent body 12 refers to the position on the non-skin side in the thickness direction with respect to the absorbent body 12 as well as the position overlapping with the absorbent body 12 in the lateral direction.

Thus, in the diaper 1, the stiffness in the lateral direction of the leg opening forming portions 60a is enhanced by the lateral welded regions 62, and the leg opening forming portions 60a are less likely to be affected by contraction in the lateral direction of the waist-circumference sections 20, 30 and the overlap portions 60b. As a result, the leg opening forming portions 60a are suppressed from contracting or curling in the lateral direction, so that the leg opening forming portions 60a are likely to be maintained in a state of having some lateral width (a wide-width state). This makes it possible to closely fit the leg opening forming portions 60a around the legs of the wearer through a face having a wide width, thereby suppressing leakage of excrement from around the legs of the wearer.

Moreover, in the diaper in the natural state (FIG. 1), since the leg opening forming portions 60a extend in the lateral direction substantially horizontally, the leg opening forming portions 60a closely fit around the legs of the wearer through face contact simply with the wearer passing his/her legs through the leg openings LH of the diaper 1. This makes such an action unnecessary as pulling out leg opening forming portions 60a that have curled inwards by using fingers, for example, thereby being able to easily wear the diaper 1 appropriately. Further, the wide-width state of the leg opening forming portions 60a is more likely to be maintained even while the diaper 1 is worn, so that the leg opening forming portions 60a closely fit around the legs of the wearer through face contact even when the sandwiching force of the legs of the wearer acts. Further, the wide width leg opening forming sections 60a closely fit the wearer, thereby being able to cover the buttocks of the wearer. Thus, there is no need to provide, for example, a cover or the like to cover the buttocks in addition to the waist-circumference sections 20, 30, enabling simple configuration of the diaper 1.

Further, in the diaper 1, the stiffness of the leg opening forming portions 60a is increased by placing the lateral welded regions 62 in the leg opening forming portions 60a. This can facilitate manufacturing of the diapers 1 more, as compared with a case in which the stiffness of the leg opening forming portions 60a is increased by respectively providing separate members onto the leg opening forming portions 60a, for example.

Further, by forming the leg-circumference extension sections 60 using the exterior sheet 14, it is possible to prevent the seams between sheets from being exposed to the non-skin-side surface in the leg opening forming portions 60a and the vicinity thereof. Further, in the diaper 1 according to an embodiment of the present disclosure, the lateral welded regions 62 are placed in the leg opening forming portions 60a and the side portions of the exterior sheet 14 are folded over to overlap. Accordingly, seams between sheets are not exposed to the laterally outer ends 60d of the leg opening forming portions 60a. Thus, in the diaper 1 according to an embodiment of the present disclosure, excrement is prevented from seeping out from seams between sheets, thereby further suppressing leakage from around the legs.

Note that the lateral welded regions 62 according to an embodiment of the present disclosure are, as illustrated in FIG. 7, formed such that dot-shaped weld portions 69 (for example, weld portions that are each formed by a protrusion in a protrusion pattern provided on the outer circumferential face of an embossing roller) are formed by being arranged in the lateral direction. Specifically, pairs of rows each having three dots of the weld portions 69 that are arranged to be inclined with respect to the lateral direction are arranged in rows in the vertical direction without being aligned with one another in the lateral direction. Similarly, the vertical welded regions 66 are also formed such that pairs of rows each having multiple of the dot-shaped weld portions 69 along the vertical direction are arranged in the lateral direction without being aligned with one another in the vertical direction. As such the welded regions 62, 66 may be obtained by being partially welded, and in this case also, the lateral stiffness of the leg opening forming portions 60a is increased. Note that it is not limited thereto and, for example, the planar shape of a single protrusion provided on the outer circumferential face of an embossing roller may be formed into the same shape as the welded regions 62, 66, such that the entire welded regions 62, 66 are welded. However, by forming each shape of the weld portions 69 to be small as in an embodiment of the present disclosure, a pressure applied when welding is likely to be constant, thereby achieving stable welding.

The predetermined lateral length of the lateral welded regions 62 maybe of any length as long as it is greater than 0 mm, however, the welded regions 62 are preferably elongated to some extent. For example, in cases in which the lateral width of the leg-circumference extension sections 60 is 40 mm, the length in the lateral direction of the lateral welded regions 62 is preferably in a range of from 7.5 mm to 27.5 mm, and is more preferably about 17.5 mm.

Moreover, the predetermined length in the lateral direction of the lateral welded regions 62 (for example, L1 in FIG. 6) indicates a length in the lateral direction from one end to the other end in the lateral direction of the lateral welded regions 62. Accordingly, the shape of the lateral welded regions 62 may be a shape extending parallel to the lateral direction (not illustrated), and may also be a shape inclined with respect to the lateral direction as in an embodiment of the present disclosure. However, for example, when the axial direction of an embossing roller corresponds to the lateral direction of the lateral welded regions 62 and the lateral welded regions 62 are parallel to the lateral direction, the lateral welded regions 62 are formed all at once. In contrast thereto, when the lateral welded regions 62 are inclined with respect to the lateral direction, each of the lateral welded regions 62 is formed by sequential application of pressure with the rotation of the embossing roller, thereby achieving stable welding.

Further, the shape of the lateral welded regions 62 is not limited to line shapes in which the dot-shaped weld portions 69 are arranged in the lateral direction as in an embodiment of the present disclosure. The lateral welded regions 62 maybe formed, for example, in a rectangular shape, trapezoidal shape, elliptical shape, barrel shape, or the like that are elongated in the lateral direction. Further, the lateral weld portions 62 are not limited to the dot-shaped weld portions 69, and the lateral welded regions 62 may be formed such that weld portions 69 of another shape, such as a square shape, a triangular shape, or the like are arranged in the lateral direction. Furthermore, a plurality of the lateral welded regions 62 may be arranged in the lateral direction in each of the leg opening forming portions 60a. The number of the lateral welded regions 62 in each of the leg opening forming portions 60a may be any as long as it is one or more.

In the diaper 1 according to an embodiment of the present disclosure, a plurality of the lateral welded regions 62 are also placed in the overlap portions 60b of the leg-circumference extension sections 60. Thus, the stiffness in the lateral direction of the overlap portions 60b is high and the overlap portions 60b are suppressed from contracting in the lateral direction. That is, a contraction force in the lateral direction from the waist-circumference sections 20, 30 is less likely to be transferred to the leg opening forming portions 60a via the overlap portions 60b. Accordingly, the leg opening forming portions 60a are further likely to be maintained in the wide-width state and the leg opening forming portions 60a can closely fit around the legs of the wearer through face contact, so that leakage from around the legs is suppressed more reliably.

As illustrated in FIG. 5, the plurality of lateral welded regions 62 are placed at constant intervals in the longitudinal direction across the entire longitudinal region of the leg-circumference extension sections 60a, thereby facilitating an adjustment to the intervals in forming the lateral welded regions 62. Accordingly, manufacture of the diaper 1 is facilitated.

However, an embodiment may be such that the lateral welded regions 62 may not be placed in the overlap portions 60b. An embodiment may also be such that the lateral welded regions 62 are placed in only one of the pair of overlap portions 60b of each of the leg-circumference extension sections 60, while no lateral welded regions 62 is placed in the other one of the overlap portions 60b. In such cases, since the number of the lateral welded regions 62, which are comparatively hard, is reduced, the burden on the skin can be reduced, which makes the diaper 1 more comfortable to wear. Further, the leg-circumference extension sections 60 do not need to have a pair of the overlap portions 60b. That is, an embodiment may be such that each of the leg-circumference extension sections 60 only overlaps with only one of the front waist-circumference section 20 and the back waist-circumference section 30, or the leg-circumference extension sections 60 overlaps with neither thereof.

Further, in the diaper 1 according to an embodiment of the present disclosure, the leak prevention wall sections 50 are also formed using the exterior sheet 14. In such a case, there are no seam in the sheet in each boundary between the leak prevention wall section 50 and the leg-circumference extension section 60, thereby being able to further suppress leakage from around the legs. For example, it is possible to prevent excrement blocked by the leak prevention wall sections 50 from seeping out from each boundary between the leak prevention wall section 50 and the leg-circumference extension section 60 to soil the legs of the wearer.

The exterior sheet 14 also extends laterally outward from a position on the non-skin-side surface side of the absorbent body 12. That is, the pair of leg-circumference extension sections 60 is formed using the shared exterior sheet 14. Accordingly, there is no seam in the exterior sheet 14 exposed to the non-skin-side surface of the absorbent main body 10, thereby suppressing leakage from a seam in the sheet. Further, the pair of leg-circumference extension sections 60 is integrally raised together when the diaper 1 is worn. Accordingly, the pair of leg-circumference extension sections 60 can closely fit around the legs of the wearer in a balanced manner, thereby suppressing leakage from around the legs.

Further, in the diaper 1 according to an embodiment of the present disclosure, the pair of leak prevention wall sections 50 is also formed using the shared exterior sheet 14. As such, the number of materials can also be reduced by forming the leg-circumference extension section 60 and the leak prevention wall section 50 on one side in the lateral direction using the single exterior sheet 14, or by respectively forming the pair of leg-circumference extension sections 60 and the pair of leak prevention wall sections 50 on two lateral sides using the single exterior sheet 14 as described above. Thus, a cost reduction can be achieved. However, it is not limited thereto. For example, the leak prevention wall section 50 and the leg-circumference extension section 60 may be formed using separate sheets, respectively, the leg-circumference extension sections 60 in a pair each may be formed using separate exterior sheets 14, or the leg-circumference extension section 60 may be formed using the liquid impermeable back sheet 13.

Moreover, as illustrated in FIG. 3, at the leg opening forming portions 60a and the overlap portions 60b in the leg-circumference extension sections 60, portions on the exterior sheet 14 where the first lateral welded regions 63 are placed (i.e., the first sheet portion 14a and the second sheet portion 14b), and portions on the exterior sheet 14 where the second lateral welded regions 64 are placed (i.e., the third sheet portion 14c and the fourth sheet portion 14d) are superimposed on each other in the thickness direction of the leg-circumference extension sections 60.

Accordingly, the lateral stiffness of the leg opening forming portions 60a and the overlap portions 60b is further increased. The exterior sheet 14 is folded into a quadruple layer to superimpose the first lateral welded regions 63 and the second lateral welded regions 64 on each other. As such, the lateral stiffness of the leg opening forming portions 60a and the overlap portions 60b is increased also with an increase in the number of stacked layers of the exterior sheet 14. Accordingly, the overlap portions 60b are further less likely to be affected by contraction of the waist-circumference sections 20, 30, and the leg opening forming portions 60*a* are more likely to be maintained in a wide-width state. This can closely fit the leg opening forming portions 60*a* around the legs of the wearer through face contact, and suppress leakage from around the legs more reliably.

In other words, with the first lateral welded regions 63 and the second lateral welded regions 64 being superimposed on each other, the stiffness of the leg opening forming portions 60*a* and the stiffness of the overlap portions 60*b* can be ensured even when the stiffness is lowered by reducing the welding strength per lateral welded region 62. Accordingly, the lateral welded regions 62 can be comparatively softened, which makes the diaper 1 more comfortable to wear. Further, it is possible to prevent the lateral welded regions 62 from becoming too thin or into holes, which results from trying to increase the welding strength so as to increase the stiffness of the lateral welded regions 62.

However, it is not limited thereto. The plurality of lateral welded regions 62 may not be superimposed on each other in the thickness direction in the leg opening forming portions 60*a* and the overlap portions 60*b*. In such a case, it is sufficient that the exterior sheet 14 is folded into a double layer and the double layer is welded to form the lateral welded regions 62. Alternatively, three of more of the lateral welded regions 62 may be superimposed on each other in the thickness direction.

Further, as illustrated in FIG. 6, the lateral welded regions are placed inside of laterally outer ends 60*d* of the leg-circumference extension sections 60 in the leg opening forming portions 60*a*. That is, the lateral welded regions 62 are absent in end portions on the laterally outer side in the leg opening forming portions 60*a*, so that these end portions are soft and accordingly comfortable to the skin of the wearer's legs contacting the end portions, which makes the diaper 1 more comfortable to wear. Further, the sandwiching force of the wearer's legs is absorbed. Thus, even while the diaper 1 is worn, the leg opening forming portions 60*a* are likely to be maintained in the wide-width state, which closely fits the leg opening forming portions 60*a* around the legs of the wearer through face contact, thereby suppressing leakage from around the legs.

Further, as illustrated in FIG. 3, in the absorbent main body 10, the back sheet 13 is disposed between the absorbent body 12 wrapped in the top sheet 11 and the exterior sheet 14 as well as between folded portions of the exterior sheet 14. As illustrated in FIG. 2, laterally outer ends 13*a* of the back sheet 13 are also disposed inside of the laterally outer ends 60*d* of the leg-circumference extension sections 60, respectively. Accordingly, the back sheet 13 is absent in the end portions on the laterally outer side in the leg opening forming portions 60*a*, so that these end portions are soft and thus comfortable to the skin of the wearer's legs contacting the end portions, which makes the diaper 1 more comfortable to wear. Further, the sandwiching force of the wearer's legs is absorbed, and thus the leg opening forming portions 60*a* are maintained in the wide-width state.

As illustrated in FIG. 2 and FIG. 3, in each of the leg opening forming portions 60*a*, four leg-circumference elastic members 61*a* to 61*d* are placed side by side in the lateral direction. Two leg-circumference elastic members 61*b*, 61*c* positioned in the center thereof intersect with the lateral welded regions 62 placed in the leg opening forming portions 60*a*. The portions where the lateral welded regions 62 are placed in the leg opening forming portions 60*a* have high stiffness, and thus are likely to be maintained in a planar shape. The portions where the lateral welded regions 62 are placed in the leg opening forming portion 60*a* are integrally raised to the wearer's side by virtue of contraction of the leg-circumference elastic members 61*b*, 61*c*. Thus, as illustrated in FIG. 7, such portions where the lateral welded regions 62 are placed in the leg opening forming portions 60*a* can closely fit around the legs of the wearer through face contact, thereby suppressing leakage from around the legs.

The leg-circumference elastic member 61*a* that is positioned on the innermost side in the lateral direction among the four leg-circumference elastic members 61*a* to 61*d* is placed at a position between the absorbent body 12 and the lateral welded regions 62 in the lateral direction. Thus, as illustrated in FIG. 7, portions laterally outside of the leg-circumference elastic members 61*a* are raised to the wearer's side by virtue of contraction of the leg-circumference elastic members 61*a*, thereby ensuring an upright height. This can make it possible to closely fit the leg opening forming portions 60*a* around the legs of the wearer.

The leg-circumference elastic member 61*d* that is positioned on the outermost side in the lateral direction among the four leg-circumference elastic members 61*a* to 61*d* is placed at the position of the laterally outer end 60*d* of each of the leg opening forming portions 60*a*. Accordingly, the leg opening forming portions 60*a* are capable of securely fitting the wearer up to the position of the laterally outer ends 60*d* by virtue of contraction of the leg-circumference elastic members 61*d*. In particular, even in a case in which the lateral welded regions 62 do not reach the laterally outer ends 60*d* in the leg opening forming portions 60*a*, the leg opening forming portions 60*a* can closely fit the wearer up to the position of the laterally outer ends 60*d*.

The overlap portions 60*b* in the leg-circumference extension sections 60 each include a non-joined region 41 (the regions 41 surrounded by bold lines in FIG. 5) where the overlap portion 60*b* and the waist-circumference section 20, 30 are not joined together in a position corresponding to the lower end portion in the vertical direction of the waist-circumference section 20, 30. A lateral welded region 62*a* is placed in the non-joined region 41.

In the overlap portions 60*b*, the non-joined regions 41 are less likely to be affected by lateral contraction of the waist-circumference sections 20, 30 than the adhesive regions 40 where the overlap portions 60*b* are joined to the waist-circumference sections 20, 30 (diagonally hatched regions in FIG. 5). Accordingly, by providing the non-joined region 41 in each boundary portion between the overlap portion 60*b* and the leg opening forming portion 60*a*, the boundary portion is likely to be maintained in the wide-width state. Moreover, by placing the lateral welded regions 62*a* in the boundary portion (the non-joined regions 41), the boundary portion is more likely to be maintained in a wide-width state. As a result, the leg opening forming portion 60*a* is also likely to be maintained in the wide-width state. In other words, the lateral contraction force from the waist-circumference sections 20, 30 is blocked by the lateral welded regions 62 in the non-joined regions 41, so that the lateral contraction force is unlikely to be transferred to the leg opening forming portions 60*a*. Consequently, the leg opening forming portions 60*a* are likely to be maintained in the wide-width state. Thus, the leg opening forming portions 60*a* can closely fit around the legs of the wearer through face contact, thereby suppressing leakage from around the legs.

In the diaper 1, in addition to the adhesive regions 40 described above, joined regions 42, 43, 44 as illustrated in FIG. 3 are also provided, where the adhesive is applied. Specifically, the first sheet portion 14*a* and the second sheet portion 14*b* of the exterior sheet 14 forming the leak prevention wall sections 50 are joined in the joined regions 42. The non-skin-side face of the absorbent body 12 wrapped in the top sheet 11, and the back sheet 13 are also joined in the joined region 43 (hereinafter also referred to as the "absorbent body joined portion 43"). The back sheet 13 and the exterior sheet 14 are also joined in the joined region 44 (hereinafter, also referred to as the "back sheet joined portion 44").

Whereas, in laterally outer portions 60c of the leg-circumference extension sections 60 illustrated in FIG. 3 (more specifically, at the portions 60c further laterally outside of the side joined portions 53 in the leak prevention wall sections 50), the first sheet portion 14a and the second sheet portion 14b of the exterior sheet 14 are not joined together with adhesive over the entire longitudinal region thereof. Similarly, the third sheet portion 14c and the fourth sheet portion 14d of the exterior sheet 14 are not joined together with adhesive over the entire longitudinal region thereof. That is, the first sheet portion 14a and the second sheet portion 14b of the exterior sheet 14 are not joined together at portions each between the first lateral welded regions 63 arranged along the longitudinal direction (for example, the portions 65 in FIG. 5), so that gaps are each created therebetween, resulting in high cushioning properties being provided. Similarly, the third sheet portion 14c and the fourth sheet portion 14d of the exterior sheet 14 are not joined together at portions each between the second lateral welded regions 64 arranged along the longitudinal direction, so that gaps are each created therebetween, resulting in high cushioning properties being provided. Accordingly, by enhancing cushioning properties of the leg-circumference extension sections 60 as such, the diaper 1 becomes more comfortable to wear.

Further, in the diaper 1 according to an embodiment of the present disclosure, since the first lateral welded regions 63 and the second lateral welded regions 64 are superimposed on each other in the thickness direction, the first sheet portion 14a and the second sheet portion 14b having high cushioning properties are further superimposed on the third sheet portion 14c and the fourth sheet portion 14d having high cushioning properties. Accordingly, the cushioning properties in the leg-circumference extension sections 60 are further enhanced.

The first vertical welded regions 67 and the second vertical welded regions 68 are also provided in the leg-circumference extension sections 60 according to an embodiment of the present disclosure. Thus, even though the first sheet portion 14a and the second sheet portion 14b are not joined together between the first lateral welded regions 63, the first sheet portion 14a and the second sheet portion 14b are firmly and closely joined together by the first vertical welded regions 67. Similarly, the third sheet portion 14c and the fourth sheet portion 14d are also firmly and closely joined together by the second vertical welded regions 68. Thus, the first sheet portion 14a and the second sheet portion 14b are not likely to separate from each other, and the third sheet portion 14c and the fourth sheet portion 14d are not likely to separate from each other, for example, even when the sheet portions are sandwiched between the wearer's legs. Accordingly, the leg opening forming portions 60a are maintained in the wide-width state. However, the first vertical welded regions 67 and the second vertical welded regions 68 may not be provided.

The lateral welded regions 62 according to an embodiment of the present disclosure are inclined with respect to the lateral direction. Accordingly, the vertical length of the non-joined portions between the first sheet portion 14a and the second sheet portion 14b when the lateral regions 62 are inclined is smaller than the vertical length of the non-joined portions, for example, when the lateral regions 62 are parallel to the lateral direction. Also, the vertical length of the non-joined portions between the third sheet portion 14c and the fourth sheet portion 14d when the lateral regions 62 are inclined is also smaller than the vertical length when the lateral regions 62 are parallel thereto. Thus, the first sheet portion 14a and the second sheet portion 14b are not likely to separate, and the third sheet portion 14c and the fourth sheet portion 14d are not likely to separate, so that the leg opening forming portions 60a are maintained in the wide-width state.

In the overlap portions 60b in the laterally outer portions 60c of the leg-circumference extension sections 60, the second sheet portion 14b of the exterior sheet 14 and the back sheet 13, and the back sheet 13 and the third sheet portion 14c of the exterior sheet 14, may not be joined together with adhesive. In particular, since the back sheet 13 and the third sheet portion 14c are not joined together, end portions that are not fixed in a stretched state of the leg-circumference elastic members 61 are able to contract. This can prevent the leg-circumference elastic members 61 from being exposed from the two longitudinal end portions of the leg-circumference extension sections 60. The third sheet portion 14c and the fourth sheet portion 14d of the exterior sheet 14 are joined to the waist-circumference sections 20, 30 through the adhesive regions 40 and the lateral welded regions 62. However, the first sheet portion 14a and the second sheet portion 14b of the exterior sheet 14 are away from the waist-circumference sections 20, 30, and thus are not likely to be affected by lateral contraction of the waist-circumference sections 20, 30. Accordingly, the leg opening forming portions 60a are likely to be maintained in the wide-width state. Even without joining the above-described portions together, the end portions on the two longitudinal ends of the leg-circumference extension sections 60 can be suppressed from being opened since the lateral welded regions 62 are placed in the overlap portions 60b.

In the leg opening forming portions 60a of the laterally outer portions 60c in the leg-circumference extension sections 60, the second sheet portion 14b of the exterior sheet 14 and the back sheet 13, and the back sheet 13 and the third sheet portion 14c of the exterior sheet 14 are preferably joined together with adhesive. With such a configuration, the four layers 14a to 14d of the exterior sheet 14 are prevented from separating from each other when being sandwiched between the wearer's legs. Thus, the leg opening forming portions 60a are maintained in the wide-width state.

As illustrated in FIG. 6, the plurality of waist-circumference elastic members 22, 32 are placed at intervals in the vertical direction in the waist-circumference sections 20, 30, and the plurality of lateral welded regions 62 are arranged at intervals in the vertical direction in the overlap portions 60b. A vertical interval L3 between the plurality of waist-circumference elastic members 22, 32 is smaller than a vertical interval L2 between the plurality of lateral welded regions 62 placed in the overlap portions 60b (L2>L3).

Accordingly, the number of the waist-circumference elastic members 22, 32 is not too small, which can ensure the fit of the waist-circumference sections 20, 30 to the wearer. That is, it is possible to ensure the fit of the waist-circumference sections 20, 30 to the wearer while suppressing lateral contraction of the overlap portions 60b and leakage from around the legs by virtue of the lateral welded regions 62. Moreover, the number of the lateral welded regions 62 placed in the overlap portions 60b is not too great, which can prevent increase in the burden on the skin caused by the comparatively hard lateral welded regions 62. Further, the overlap portions 60b can be prevented from being torn from the lateral welded regions 60b due to the intervals between the lateral welded regions 62 being too small.

However, the configuration is not limited to the above. The vertical interval L2 of the lateral welded regions 62 placed in the overlap portions 60b may be equal to or smaller than the vertical interval L3 of the waist-circumference elastic members 22, 32. In such a case, the number of the lateral welded regions 62 is increased, so that lateral contraction of the overlap portions 60b is suppressed more reliably. The above comparison may be made using an interval between the waist-circumference elastic members 22, 32 located at the same vertical position as the position of the overlap portions 60b, or using an interval between the waist-circumference elastic members 22, 32 located above the overlap portions 60b. In cases in which the intervals between the lateral welded regions 62 and the intervals between the waist-circumference elastic members 22, 32 are not constant, the intervals therebetween maybe any intervals as long as at least one of the intervals between the waist-circumference elastic members 22, 32 is smaller than at least one of the intervals between the lateral welded regions 62.

The lateral welded regions 62 placed in the overlap portions 60b are preferably not superimposed on the waist-circumference elastic members 22, 32 in plan view in the thickness direction of the leg-circumference extension sections 60 (FIG. 6). That is, the lateral welded regions 62 preferably deviate in the vertical direction from the waist-circumference elastic members 22, 32. This can prevent contraction in portions of the waist-circumference elastic members 22, 32 that are overlapped with the overlap portions 60b from being excessively suppressed by the lateral welded regions 62, so that such portions of the waist-circumference elastic members 22, 32 contract appropriately. Accordingly, it is possible to effectively utilize the waist-circumference elastic members 22, 32 and ensure the fit of the waist-circumference sections 20, 30 to the wearer. However, it is not limited thereto. The vertical positions of some or all of the plurality of lateral welded regions 62 may coincide with vertical positions of the waist-circumference elastic members 22, 32.

As illustrated in FIG. 6, waist-circumference elastic members 22a, 32a located above the absorbent body 12 in the vertical direction extend continuously from one side portion to the other side portion in the lateral direction of the waist-circumference section 20, 30. In contrast, waist-circumference elastic members 22b, 32b located at the same vertical position as the absorbent body 12 each include a portion from one side portion in the lateral direction of the waist-circumference section 20, 30 to one side portion in the lateral direction of the absorbent body 12, and a portion from the other side portion in the lateral direction of the absorbent body 12 to the other side portion in the lateral direction of the waist-circumference section 20, 30. That is, the waist-circumference elastic members 22b, 32b each include a discontinuous portion in a position superimposed on the absorbent body 12 in the thickness direction of the waist-circumference section 20, 30 (for example, from point a to point b in FIG. 6).

Thus, the absorbent body 12 is not likely to be affected by lateral contraction of the waist-circumference elastic members 22, 32, thereby being able to suppress the absorbent body 12 from be twisted. This causes the absorbent body 12 to closely fit the wearer such that excrement is properly absorbed by the absorbent body 12, thereby suppressing leakage from around the legs. Since the absorbent body 12 is suppressed from being twisted, the leg opening forming portions 60a can be extended substantially horizontally to the lateral direction. This can closely fit the leg opening forming portions 60a around the legs of the wearer through face contact, thereby suppressing leakage from around the legs.

Modified Examples

Figure 9A:
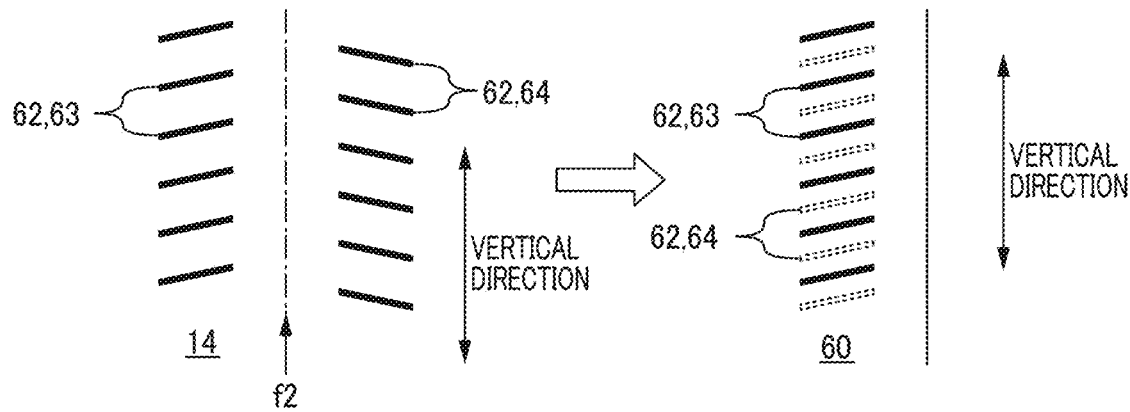
FIG. 9A to FIG. 9C are diagrams to explain modified examples of the lateral welded regions 62.
Figure 9B:
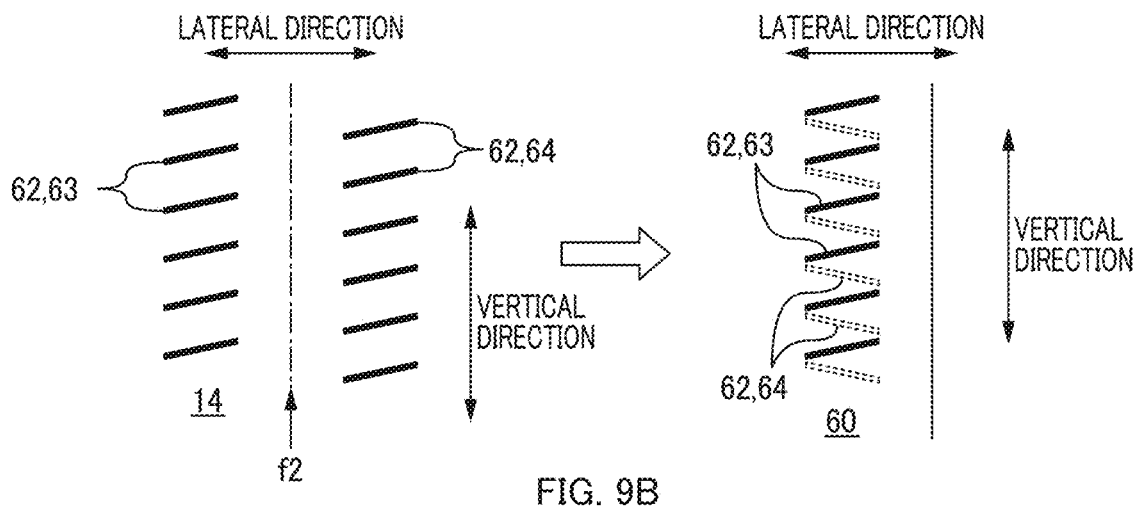
Figure 9C:
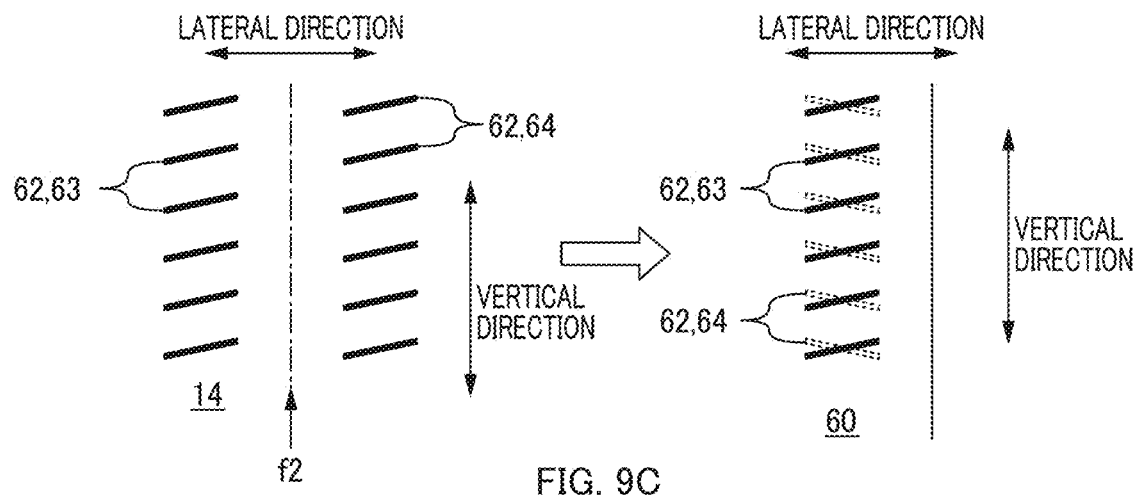

FIG. 9A to FIG. 9C are diagrams for explaining modified examples of the lateral welded regions 62. Diagrams on the left side of FIG. 9A to FIG. 9C illustrate a state in which the first lateral welded regions 63 and the second lateral welded regions 64 have been formed in the exterior sheet 14 during manufacture of the diaper 1. The diagrams on the right side illustrate positional relationships between the first lateral welded regions and the second lateral welded regions 64 in the leg-circumference extension sections 60.

In an embodiment described above, the first lateral welded regions 63 and the second lateral welded regions 64 are formed symmetrically with respect to the fold position f2 of the exterior sheet 14, as illustrated in FIG. 4, that is, their inclination directions are symmetrical to each other and vertical positions match each other. Accordingly, in each of the leg opening forming portions 60a and the overlap portions 60b, the first lateral welded regions 63 and the second lateral welded regions 64 are placed so as to be superimposed on each other in the thickness direction. However, it is not limited thereto. Some or all of the first lateral welded regions 63 and the second lateral welded regions 64 may not be superimposed on each other in plan view in the thickness direction. That is, in each of the leg opening forming portions 60a and the overlap portions 60b, the positions in a flat plane (the positions in the lateral direction and the vertical direction) of the first lateral welded regions 63 may deviate from the positions in a flat plane of the second lateral welded regions 64.

For example, as illustrated on the left side in FIG. 9A, the first lateral welded regions 63 and the second lateral welded regions 64 may be formed such that their inclination directions are symmetrical with respect to the fold position f2 and their positions deviate from each other in the vertical direction. In such a case, as illustrated on the right side of FIG. 9A, the first lateral welded regions 63 and the second lateral welded regions 64 that are inclined in the same direction as each other are arranged alternately in the vertical direction in plan view of the leg-circumference extension sections 60.

For example, as illustrated on the left side of FIG. 9B, the first lateral welded regions 63 and the second lateral welded regions 64 may be formed such that their inclination directions thereof are the same with respect to the fold position f2 and their positions deviate from each other in the vertical direction. In such a case, as illustrated on the right side of FIG. 9B, the first lateral welded regions 63 and the second lateral welded regions 64 that are inclined in directions reverse to each other are arranged alternately in the vertical direction in plan view of the leg-circumference extension sections 60.

For example, as illustrated on the left side of FIG. 9C, the first lateral welded regions 63 and the second lateral welded regions 64 may be formed such that their inclination directions are the same with respect to the fold position f2 and their positions are the same in the vertical direction. In such a case, as illustrated on the right side of FIG. 9C, the first lateral welded regions 63 and the second lateral welded regions 64 that are inclined in directions reverse to each other are arranged so as to intersect each other in plan view of the leg-circumference extension sections 60.

As illustrated in FIG. 9A and FIG. 9B, the first lateral welded regions 63 and the second lateral welded regions 64 may completely deviate from each other, or alternatively, as illustrated in FIG. 9C, a portion of each first lateral welded region 63 and a portion of each second lateral welded region 64 may be superimposed on each other, while the remaining portions thereof may deviate from each other. Accordingly, since the first lateral welded regions 63 and the second lateral welded regions 64 deviate from each other in plan view in the thickness direction, the lateral welded regions 62 are present in a wider range of a flat plane in the leg opening forming portions 60a and the overlap portions 60b, thereby enhancing lateral stiffness of the leg opening forming portions 60a and the overlap portions 60b. Thus, the overlap portions 60b are less likely to be affected by lateral contraction of the waist-circumference sections 20, 30, so that the leg opening forming portions 60a are likely to be maintained in the wide-width state, thereby suppressing leakage from around the legs.

As illustrated in FIG. 9A and FIG. 9B, in a case in which the first lateral welded regions 63 and the second lateral welded regions 64 completely deviate from each other, the lateral welded regions 62 are formed by sequentially applying pressure with rotation of an embossing roller, for example, when welding is performed. This results in stable welding. Further, although not illustrated, some of the plurality of first lateral welded regions 63 may be superimposed on the second lateral welded regions 64, and the remaining first lateral welded regions 63 may not be superimposed on the second lateral welded regions 64. Further, the size and the shape in plan view of the first lateral welded regions 63 may also be different from those of the second lateral welded regions 64, and the size and the shape in plan view maybe different among the first lateral welded regions 63 and/or among the second lateral welded regions 64. Further, the first lateral welded regions 63 and the second lateral welded regions 64 may also be different in arrangement between in the overlap portions 60b and in the leg opening forming portions 60a. Further, the number of the first lateral welded regions 63 may be different from the number of the second lateral welded regions 64. For example, the number of the second lateral welded regions 64 on the non-skin side is made greater than the number of the first lateral welded regions 63 on the skin side, thereby being able to enhance the comfort to the skin while enhancing the lateral stiffness of the leg-circumference extension sections 60.

Method of Manufacturing Absorbent Main Body 10

Figure 10:
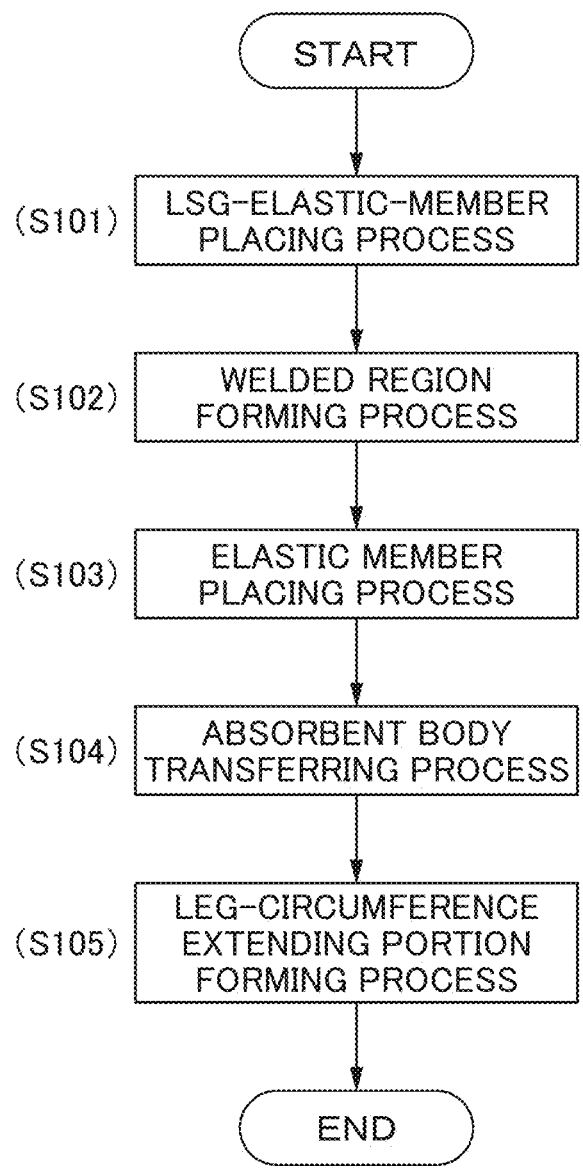
FIG. 10 is a diagram to illustrate a flow of manufacturing the absorbent main body 10.

A description will now be given of a specific method for manufacturing the absorbent main body 10 including the pair of leak prevention wall sections 50 and the pair of leg-circumference extension sections 60. FIG. 10 is a diagram illustrating a flow of manufacturing the absorbent main body 10. The diaper 1 according to an embodiment of the present disclosure is continuously manufactured on a manufacturing line by executing the processes of S101 to S105 illustrated in FIG. 10.

In an embodiment of the present disclosure, the processes of S101 to S105 are executed while a base sheet of the absorbent main body 10 is being transported at a predetermined transport speed along a predetermined transport direction. The "base sheet of the absorbent main body 10" means an exterior continuous sheet 141 configured such that a plurality of the exterior sheets 14 continues in the longitudinal direction (vertical direction) in FIG. 2, and a direction in which this exterior continuous sheet 141 is transported along the longitudinal direction results in a transport direction. In the following description, a direction along the transport direction (i.e., the longitudinal direction of the exterior sheet 14) is referred to as the MD direction (corresponding to the vertical direction), and a direction orthogonal to the MD direction is referred to as the CD direction (corresponding to the lateral direction).

(S101)

Figure 11:
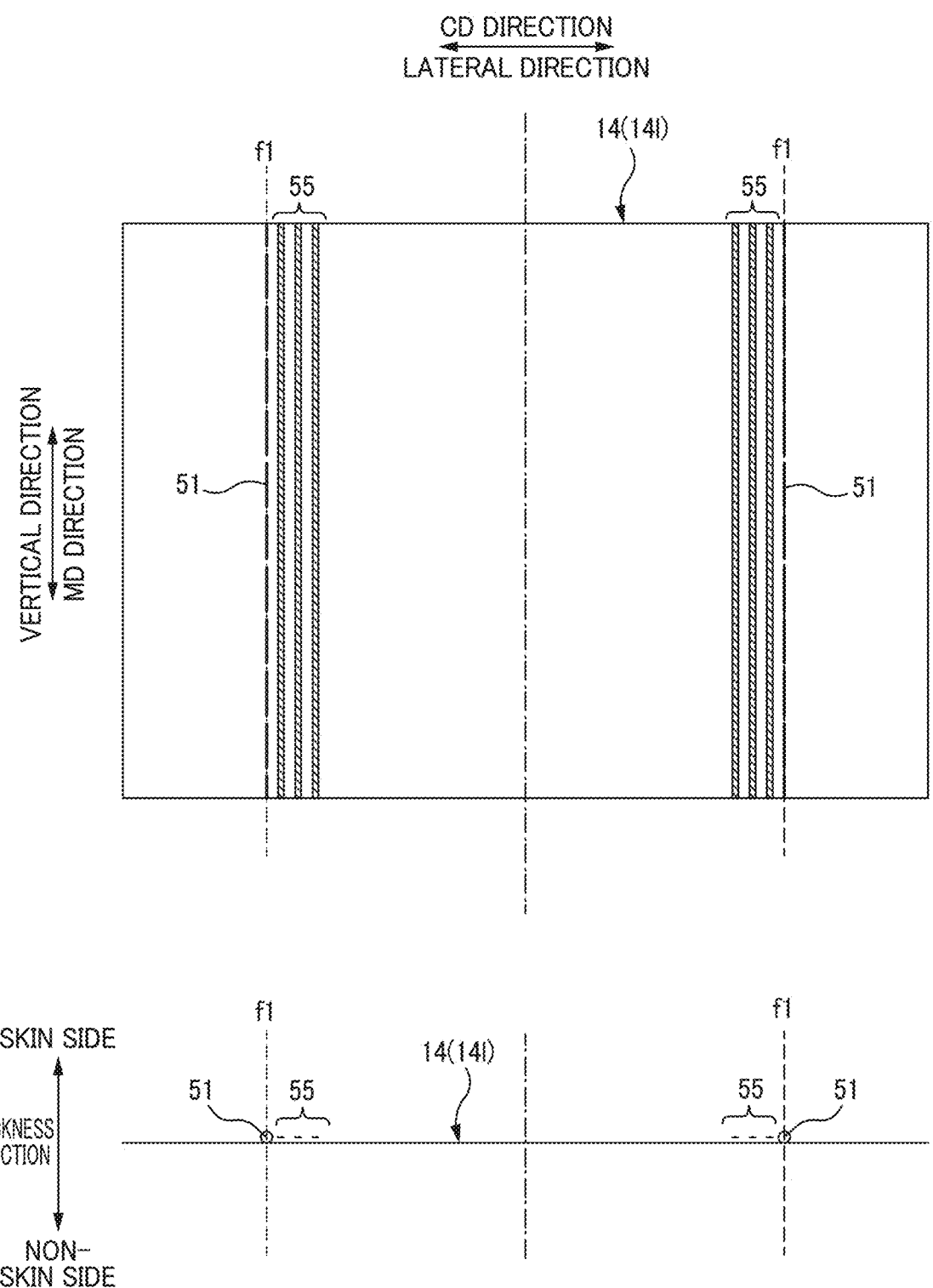
FIG. 11 is a plan view and a cross-section to explain an LSG elastic member placing process.

First, an LSG elastic member placing process is performed to place the LSG elastic members 51 of the leak prevention wall sections 50 described above onto the base sheet (the exterior sheet 14) that is transported along the MD direction (S101). FIG. 11 is a plan view and a cross-section to explain the LSG elastic member placing process. The exterior sheet 14 in an unfolded state is illustrated in FIG. 11. In order to simplify the description, FIG. 11 illustrates a state of the above-described exterior sheets 14 obtained by cutting the exterior continuous sheet 141 into product (diaper 1) units. The same applies to FIG. 12 to FIG. 16 as will be described below.

As illustrated in FIG. 11, in the LSG elastic member placing process (S101), the LSG elastic members 51 in a state of being stretched in the MD direction (vertical direction) are placed along the MD direction at the predetermined positions f1 (the above-described fold positions f1) on both sides in the CD direction (lateral direction) of the exterior sheet 14 (the exterior continuous sheet 141). An adhesive such as a hot melt adhesive (HMA) or the like is applied onto the surface of the LSG elastic members 51, and the LSG elastic members 51 are joined to the exterior sheet 14 with the adhesive. Accordingly, stretchability in the vertical direction (longitudinal direction) is exhibited at the portions where the LSG elastic members 51 are joined at the predetermined positions f1 in the exterior sheet 14. This can raise the leak prevention wall sections 50 to the wearer's skin side when the diaper 1 has been formed into a pants shape.

Further, in S101, LSG adhesion portions 55 are also formed, by providing (applying) the adhesive (for example, the hot melt adhesive HMA) along the MD direction as illustrated in FIG. 11 in respective regions inside in the CD direction (lateral direction) of the predetermined positions f1. The LSG adhesion portions 55 are adhesion portions for joining portions of the folded exterior sheet 14 together in the thickness direction when the exterior sheet 14 is folded back on itself at the predetermined positions f1, in the next process (S102). The LSG adhesion portions 55 may be formed prior to placing the LSG elastic members 51.

(S102)

Figure 12:
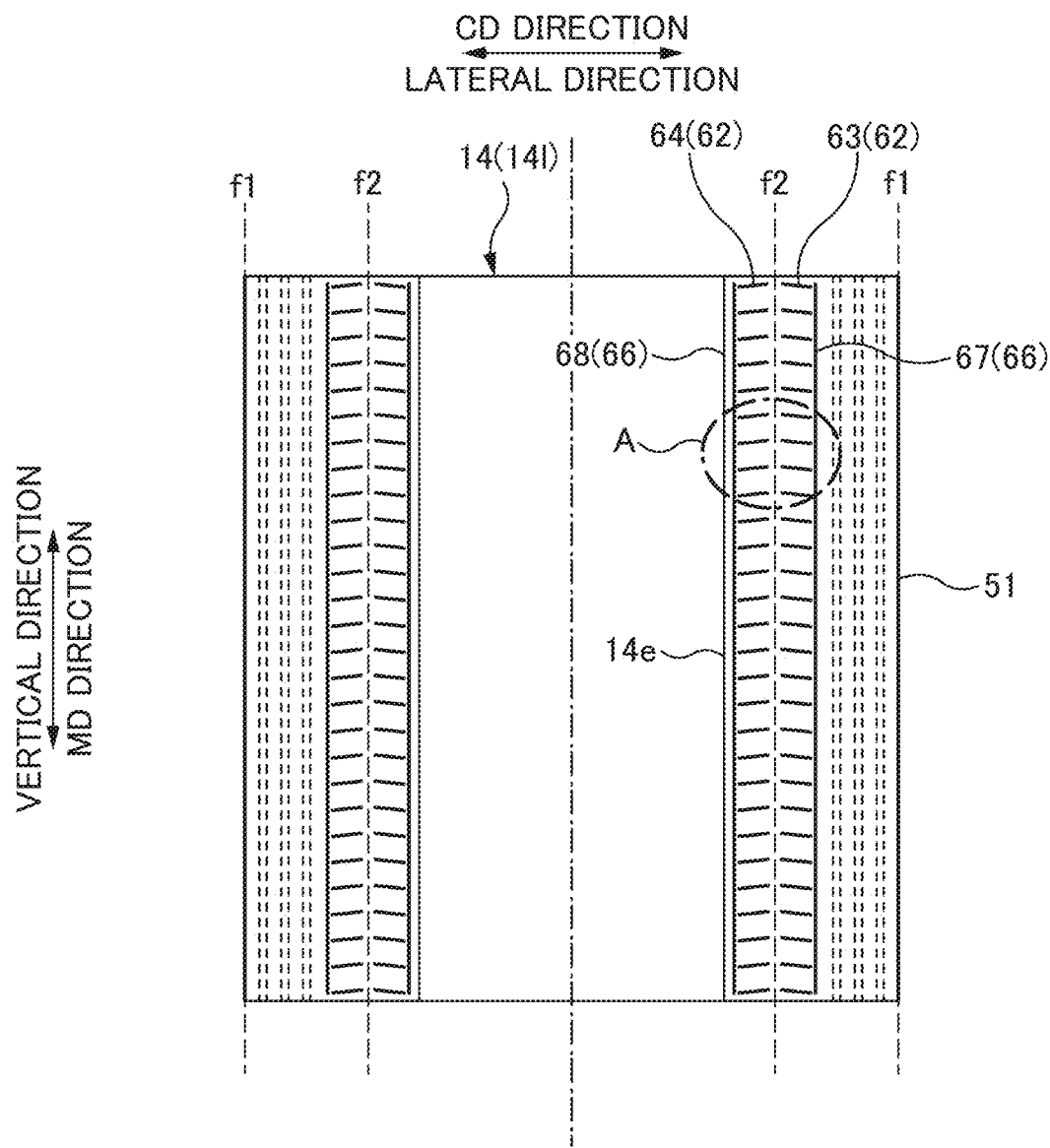
FIG. 12 is a plan view and a cross-section to explain a welded region forming process.
Figure 12:
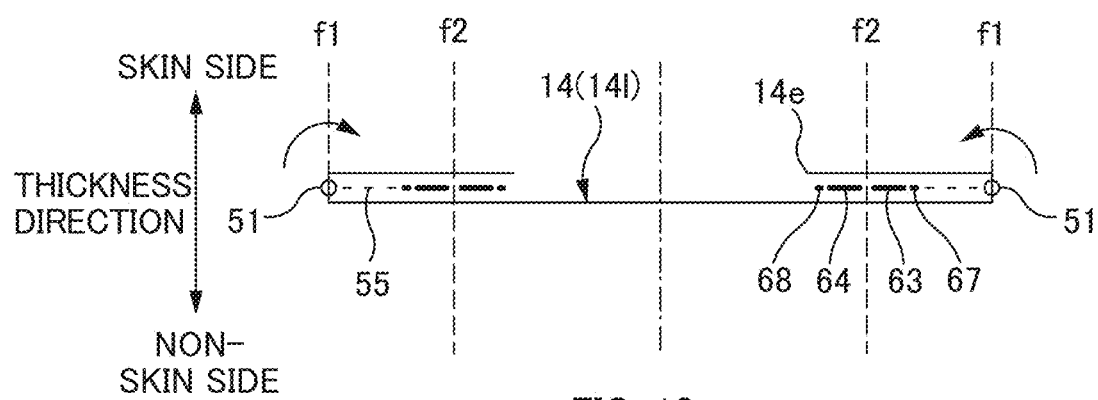
Figure 13:
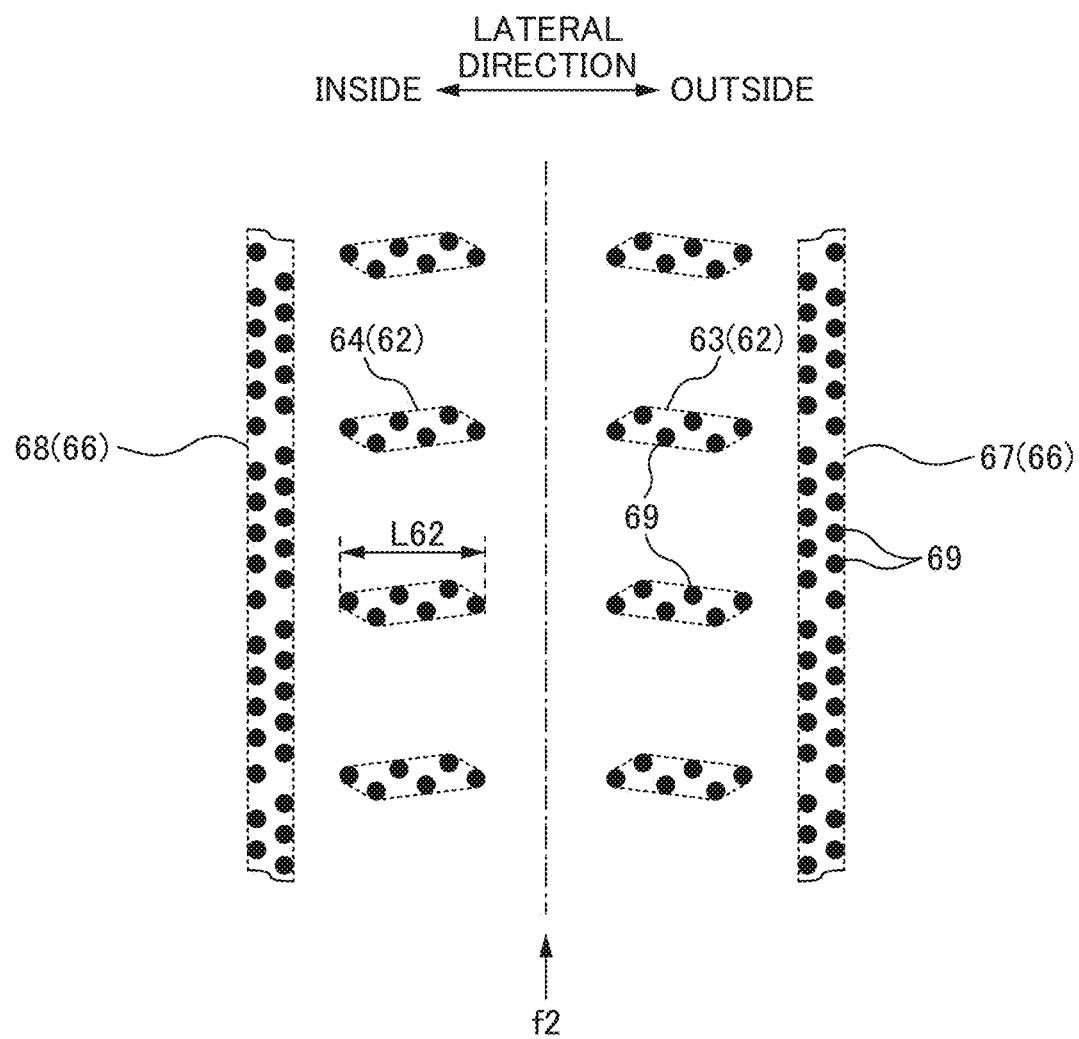
FIG. 13 is an enlarged diagram illustrating a region A in FIG. 12.

Next, a welded region forming process (S102) is performed such that the two end portions in the CD direction (lateral direction) of the exterior sheet 14 (the exterior continuous sheet 141) in the unfolded state are folded back on themselves from the outside toward the inside, and the lateral welded regions 62 and the vertical welded regions 66 are formed at portions where the exterior sheet 14 is superimposed by being folded on itself in the thickness direction. FIG. 12 is a plan view and a cross-section to explain the welded region forming process. FIG. 13 is an enlarged view of a region A in FIG. 12 and is a diagram for explaining the lateral welded regions 62 and the vertical welded regions 66.

In the welded region forming process (S102), first, the two end portions of the exterior sheet 14 are folded back on themselves from the outside toward the inside in the CD direction (lateral direction) at the predetermined positions f1 where the LSG elastic members 51 (the LSG elastic members) are placed which serve as folding positions. That is, the exterior sheet 14 is folded over on itself in the thickness direction, at the positions f1 where the LSG elastic members 51 are provided, which serve as bases for folding back, so as to sandwich the LSG elastic members 51, and is joined with the LSG adhesion portions 55. Such joined portions are portions configured to be raised as the leak prevention wall sections 50 when the diaper 1 is worn. The strength of the leak prevention wall sections 50 is ensured with the portions of the folded and superimposed exterior sheet 14 being joined together, so that the leak prevention wall sections 50 are likely to be suppressed from falling over or collapsing in shape. Note that, when the exterior sheet 14 is folded back, used is a fold-back mechanism (sealer) which is configured to fold back the exterior continuous sheet 141 in the CD direction while being transported along the MD direction. In an embodiment of the present disclosure, the adhesive is not likely to adhere to the sealer since the LSG adhesion portions 55 are formed inside in the CD direction (lateral direction) of the predetermined positions f1. This reduces the need to stop the manufacturing line in order to clean the sealer or perform maintenance or the like, thereby being able to efficiently manufacture the diapers 1.

Then, the lateral welded regions 62 and the vertical welded regions 66 are formed by partially welding regions located inside in the lateral direction of the regions that have been joined using the LSG adhesion portions 55 in the portions where the exterior sheet 14 has been folded and superimposed on itself. The portions where the welded regions 62, 66 are formed correspond to portions that extend in the lateral direction around the leg-circumference of the wearer, serving as the leg-circumference extension sections 60 when the diaper 1 is worn. By forming the welded regions 62, 66 to have predetermined lateral and vertical lengths, it is possible to enhance the lateral and vertical stiffness of the leg-circumference extension sections 60 that are formed using the exterior sheet 14.

As illustrated in FIG. 13, in an embodiment of the present disclosure, the welded regions 62, 66 are formed in the exterior sheet 14 folded into a double layer in the thickness direction, such that the plurality of first lateral welded regions 63 are formed to be arranged in rows at intervals in the longitudinal direction in each portion on the laterally outer side, and the plurality of second lateral welded regions 64 are formed to be arranged in rows at intervals in the longitudinal direction in each portion on the laterally inner side relative to the first lateral welded regions 63 across the predetermined position f2 (the above-described fold position f2). That is, the first lateral welded regions 63 and the second lateral welded regions 64 are discontinuous to each other in the lateral direction, and the first lateral welded regions 63 and the second lateral welded regions 64 are formed so as not to overlap with the predetermined position f2 in the lateral direction. This can suppress increase in the stiffness of the predetermined positions f2, thereby being able to tightly folding back when the exterior sheet 14 is folded back on itself at each predetermined position f2 in an extension section forming process (S105) which will be described later.

Further, the first vertical welded regions 67 are formed outside in the lateral direction of the first lateral welded regions 63, and the second vertical welded regions 68 are formed inside in the lateral direction of the second lateral welded regions 64. Note that the lateral welded regions 62 and the vertical welded regions 66 are formed so as not to overlap with ends 14e constituting edges of the exterior sheet 14 in the lateral direction (see FIG. 12). This suppresses these edge portions (14e) from increasing in stiffness and the sheet member from becoming hard, thereby preventing degradation in texture even in cases where the edge portions are pressed against the skin of the wearer when the diaper 1 is worn.

The lateral welded regions 62 (63, 64) are formed such that multiple of the dot-shaped weld portions 69 are formed to be arranged in the lateral direction. Specifically, pairs of rows each having three dots of the weld portions 69 arranged to be inclined with respect to the lateral direction are arranged in rows in the vertical direction without being aligned with one another in the lateral direction. Similarly, the vertical welded regions 66 (67, 68) are also formed such that pairs of rows each having multiple of the dot-shaped weld portions 69 along the vertical direction are arranged in the lateral direction without being aligned with one another in the vertical direction. Each of the weld portions 69 is formed, for example, by a welding means such as ultrasonic welding or the like by employing an embossing roller having its rotational axis set along the CD direction and using a single projection in a projection pattern provided on the outer circumferential face of the embossing roller. However, the weld portions 69 may also be formed using another welding means, such as heat welding, laser illumination, or the like.

Accordingly, such welded regions 62, 66 may be obtained by being partially welded using the dot-shaped weld portions 69, thereby being able to reduce the area of each weld portion 69. This makes it possible to concentrate and repeatedly apply ultrasonic vibrations or the like onto individual points using a projection pattern during welding, thereby being able to perform stable welding. However, the shapes of the welded regions 62, 66 are not limited thereto and, for example, the planar shape of a single protrusion provided on the outer circumferential face of an embossing roller may be formed into the same shape as the welded regions 62, 66, such that the entire welded regions 62, 66 are welded. That is, the welded regions 62, 66 may be formed in linear shapes in which the entire regions surrounded by dashed lines in FIG. 13 are welded.

Moreover, the predetermined length in the lateral direction of the lateral welded regions 62 indicates a length in the lateral direction from one end to the other end in the lateral direction of the lateral welded regions 62, and is indicated by L62 in FIG. 13. As long as the shape of the lateral welded regions 62 has a predetermined length (L62) in the lateral direction (CD direction), the shape of the lateral welded regions 62 may be a shape extending parallel to the lateral direction (not illustrated), and may also be a shape inclined with respect to the lateral direction as in an embodiment of the present disclosure.

However, in a case where the projection pattern of the embossing roller is arrayed parallel to the CD direction and the lateral welded regions 62 are formed parallel to the CD direction, the lateral welded regions 62 along the CD direction (lateral direction) is formed at the same instant and timing at which a row in the projection pattern contacts the exterior sheet 14 (the exterior continuous sheet 141) along with the rotation of the embossing roller. In such cases, it is difficult to apply uniform pressure over the entire regions in the lateral direction, and thus the welding strength might be uneven in the lateral direction of the lateral welded regions 62. Further, the projection pattern is likely to be worn out due to a large pressure being applied all at once to a row of the projection pattern. In contrast thereto, when the lateral welded regions 62 are inclined with respect to the lateral direction (CD direction), the lateral welded regions 62 are formed while the point to which pressure is applied is being sequentially shifted along with the rotation of the embossing roller, so that local welding defects or the like are less likely to occur and the welding strength is less likely to be uneven. Moreover, since the place to which pressure is applied is sequentially shifted, the projections provided on the outer circumferential face of the embossing roller are less likely to be worn out, thereby being able to efficiently perform manufacturing.

The predetermined lateral length of the lateral welded regions 62 maybe of any length as long as it is greater than 0 mm, however the welded regions 62 are preferably elongated to some extent. For example, in cases in which the lateral width of the leg-circumference extension sections 60 is 40 mm, the length in the lateral direction of the lateral welded regions 62 is preferably in a range of from 7.5 mm to 27.5 mm, and is more preferably about 17.5 mm.

(S103)

Figure 14:
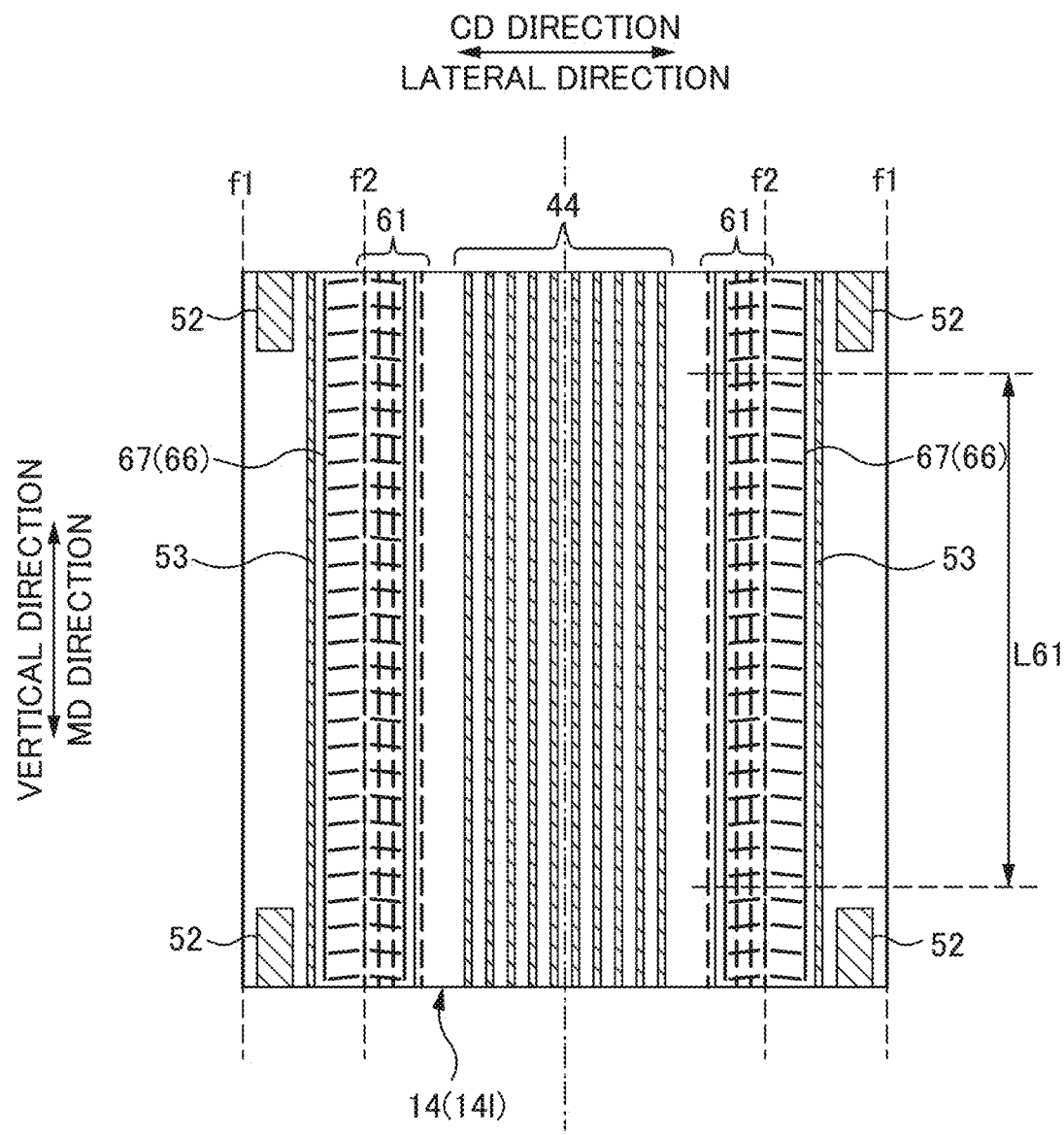
FIG. 14 is a plan view and a cross-section to explain an elastic member placing process.
Figure 14:
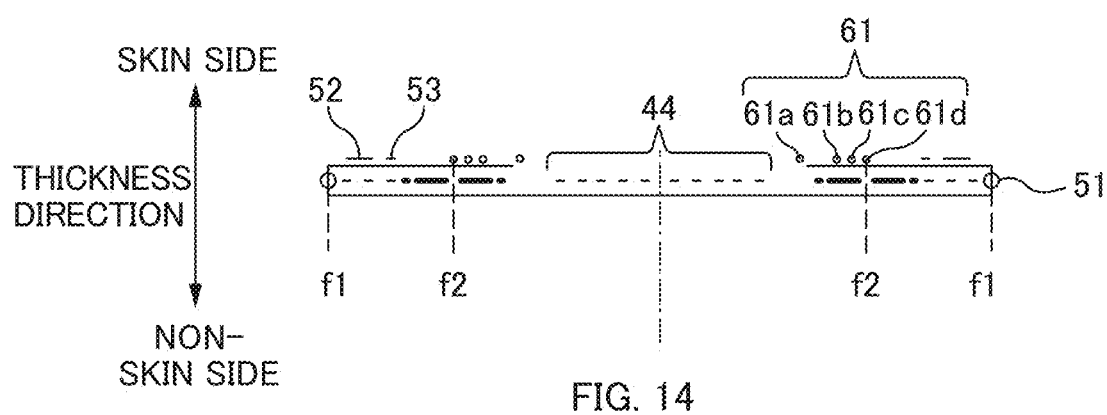

An elastic member placing process (S103) is then performed in which the leg-circumference elastic members 61 are placed in a predetermined region of the exterior sheet 14 (the exterior continuous sheet 141). FIG. 14 is a plan view and a cross-section to explain the elastic member placing process.

First, an adhesive for forming the end joined portions 52 and the side joined portion 53 of the leak prevention wall sections 50 is applied to in the portions in the lateral direction (CD direction) outside of the lateral welded regions 62 and the vertical welded regions 66 on the skin side face of the double-layered exterior sheet 14. In an embodiment of the present disclosure, as illustrated in FIG. 14, the side joined portions 53 are formed further outside in the lateral direction of the first vertical welded region 67 that is formed outermost in the lateral direction. That is, the side joined portions 53 are formed so as not to overlap with at least the welded regions 62, 63 in the lateral direction. Adhesive for forming the back sheet joined portion 44 to join the back sheet 13 in the next process (S104) may also be applied to a central region in the lateral direction (CD direction) on the skin side face of the exterior sheet 14 in this process (see FIG. 14). The order in which the joined portions 44, 52, 53 are formed may be freely selected. However, these joined portions are formed in positions on the skin side face of the exterior sheet 14 that do not interfere with each other, and thus the adhesive can be applied thereto at the same time. Application of the adhesive at the same time can reduce the manufacturing cost while making the facility space of the manufacturing line more compact.

After the joined portions 44, 52, 53 are formed, the plurality of leg-circumference elastic members 61 in a stretched state along the vertical direction (MD direction) are joined to portions inside in the lateral direction (CD direction) of the side joined portions 53 on the skin side face of the exterior sheet 14. Note that the leg-circumference elastic members 61 is applied with the adhesive in advance in the range of a region L61 illustrated in FIG. 14, thereby providing stretchability in the vertical direction (MD direction) to the exterior sheet 14 in the range of this region L61. Accordingly, stretchability in the vertical direction is exhibited at least in the range of the region L61 in the leg-circumference extension sections 60, thereby improving the fit of the leg-circumference extension sections 60 around the legs of the wearer when the diaper 1 is worn.

In an embodiment of the present disclosure, four leg-circumference elastic members 61*a* to 61*d* from the inside to the outside in the lateral direction are provided. From thereamong, the leg-circumference elastic members 61*b* and 61*c* are placed so as to overlap with the lateral welded regions 64 (62) in the lateral direction. The leg-circumference elastic member 61*a* located innermost in the lateral direction is placed at a position between the absorbent body 12 and the lateral welded regions 62 in the lateral direction. The leg-circumference elastic member 61*d* located outermost in the lateral direction is placed at the predetermined position f2 in the lateral direction. The predetermined position f2 is the position corresponding to the laterally outer end 60*d* of each of the leg-circumference extension sections 60 when the diaper 1 has been formed into a pants shape.

In the manufacturing method according to an embodiment of the present disclosure, the leg-circumference elastic members 61 are placed in S103 after the lateral welded regions 62 are formed at S102, thereby being able to cause a stretching force in the vertical direction by virtue of the leg-circumference elastic members 61 to act on the regions where the lateral welded regions 62 (64) are formed in the leg-circumference extension sections 60. If the lateral welded regions 62 are formed after placing the leg-circumference elastic members 61, the leg-circumference elastic members 61 might be cut by the pressure from the embossing roller or the like that is applied when the lateral welded regions 62 are formed, such that a stretching force might no longer be exhibited in the leg-circumference extension sections 60. In contrast thereto, according to the manufacturing method of an embodiment of the present disclosure, it is possible to form the lateral welded regions 62 in regions overlapping with the leg-circumference elastic members 61 without impairing the stretching force of the leg-circumference elastic members 61. The effect of placing the leg-circumference elastic members 61 and the lateral welded regions 62 so as to overlap with each other in the leg-circumference extension sections 60 will be described later.

(S104)

Figure 15:
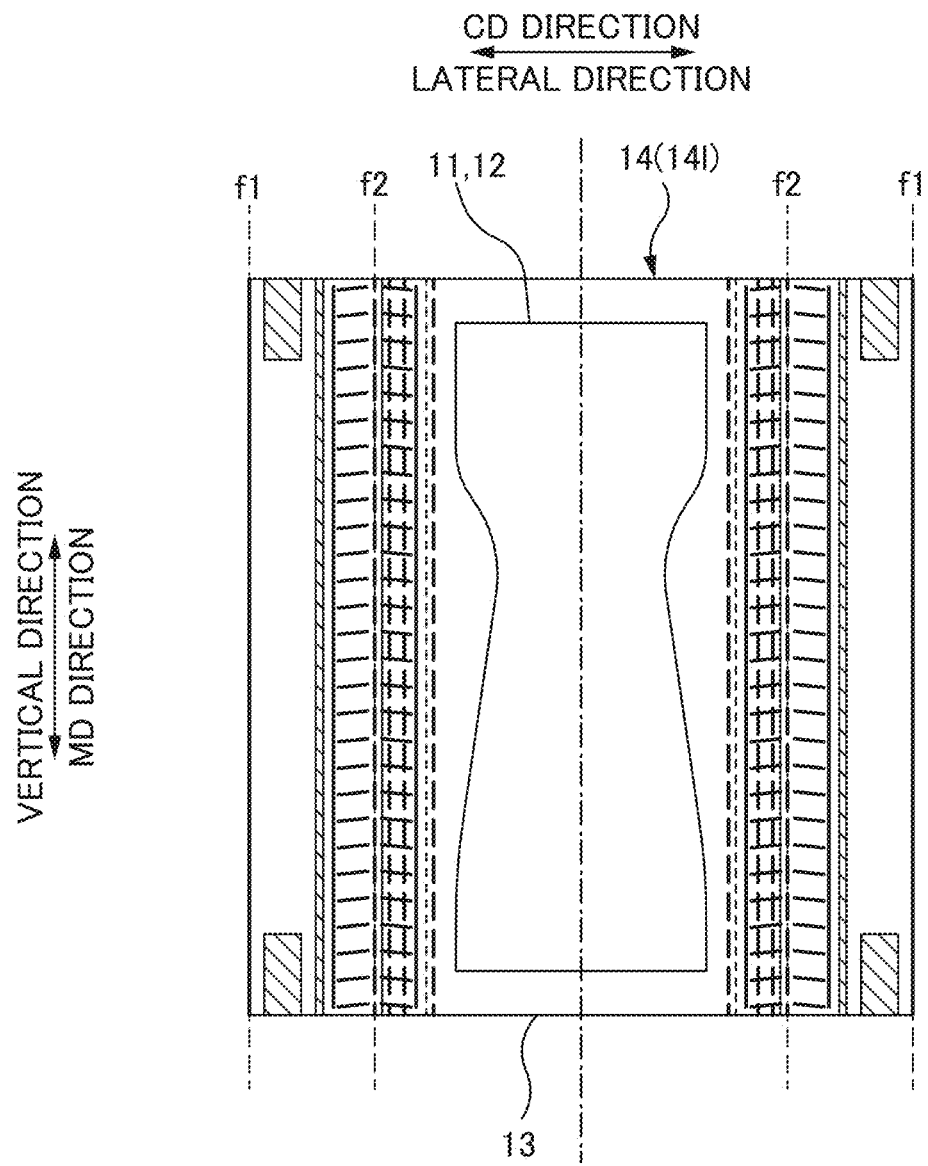
FIG. 15 is a plan view and a cross-section to explain an absorbent body transferring process.

Next, an absorbent body transferring process (S104) is performed in which the absorbent body 12 (the absorbent body 12 wrapped in the top sheet 11) is attached to the skin side of the exterior sheet 14 (the exterior continuous sheet 141). FIG. 15 is a plan view and a cross-section to explain the absorbent body transferring process.

First, the back sheet 13 is joined to the skin side face of the exterior sheet 14. The back sheet 13 is placed so as to overlap with the leg-circumference elastic members 61*a* to 61*c* in the lateral direction (CD direction). That is, the back sheet 13 is placed so as to cover at least a region between the leg-circumference elastic member 61*c* placed on one side in the lateral direction and the leg-circumference elastic member 61*c* placed on the other side in the lateral direction, from the skin side in the thickness direction, and the back sheet 13 is joined to the skin side face of the exterior sheet 14 with the back sheet joined portion 44 and the adhesive applied to the surface of the leg-circumference elastic members 61.

Note that the back sheet 13 can also be placed further on the non-skin side with respect to the leg-circumference elastic members 61 in view of the configuration of the absorbent main body 10. However, in such cases, a portion of the leg-circumference elastic members 61 might be exposed to the skin side, and thus the adhesive applied onto the surface of the leg-circumference elastic members 61 might adhere to the wearer's body or the like when the diaper 1 is worn, which might cause discomfort to the wearer. In contrast thereto, in the diaper 1 according to an embodiment of the present disclosure, the back sheet 13 is placed so as to cover the skin side of the leg-circumference elastic members 61*a* to 61*c* in S104, thereby suppressing the leg-circumference elastic members 61 from being exposed to the skin side, so that the adhesive is less likely to adhere to the wearer's body while the diaper 1 is worn.

Then, the absorbent body 12 is joined (transferred) to the skin side face of the back sheet 13 through the absorbent body joined portion 43 that is formed with the adhesive applied to the skin side face of the back sheet 13.
(S105)

Figure 16:
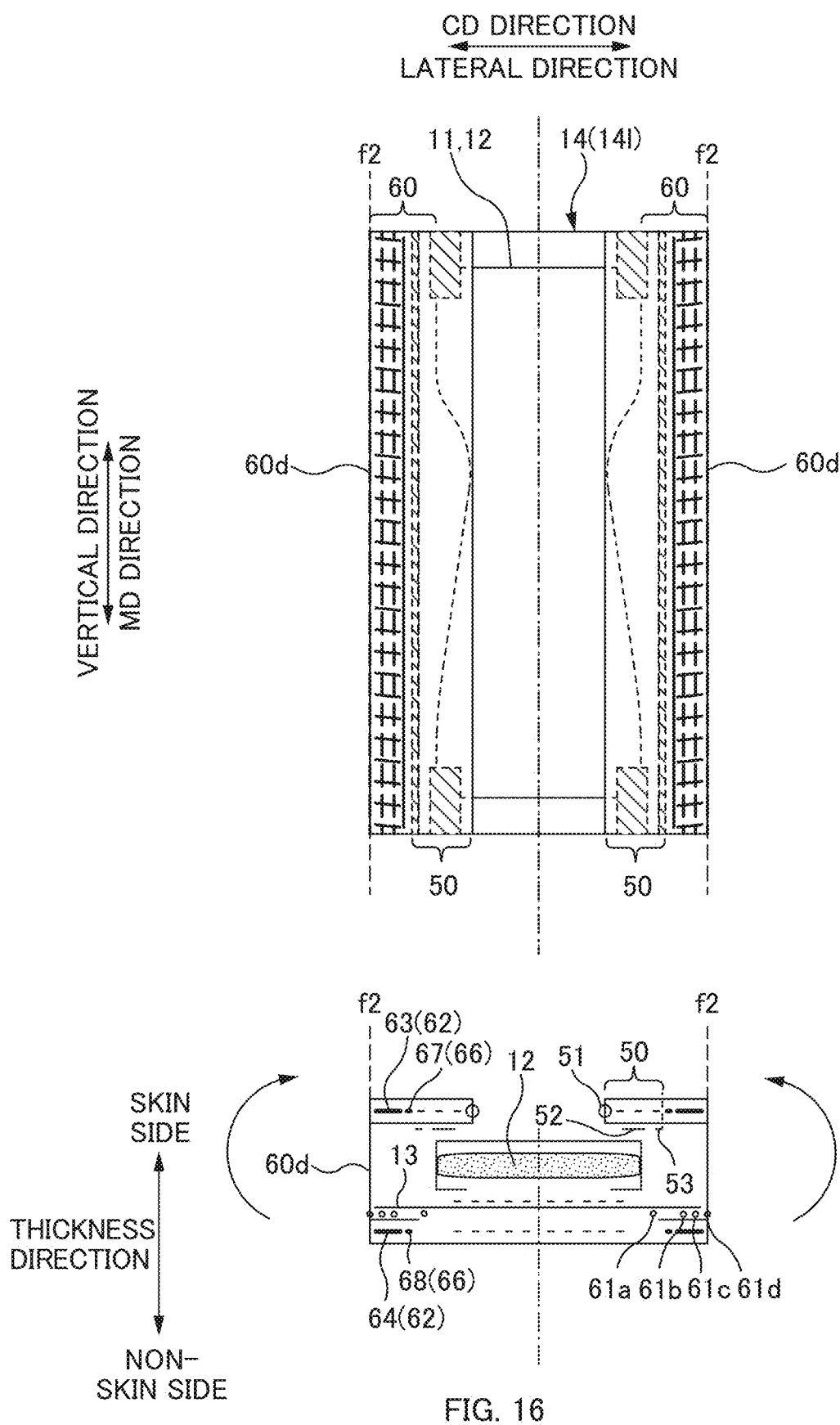
FIG. 16 is a plan view and a cross-section to explain a leg-circumference extension section forming process.

Next, a leg-circumference extension section forming process (S105) is performed in which the leg-circumference extension sections 60 are formed by folding the two lateral end portions of the exterior sheet 14 (the exterior continuous sheet 141) back on themselves once again from the outside to the inside. FIG. 16 is a plan view and a cross-section to explain the leg-circumference extension section forming process. The cross-section in FIG. 16 corresponds to FIG. 3.

In the extension section forming process (S105), the two end portions of the exterior sheet 14 are folded back on themselves from the outside toward the inside in the lateral direction at the predetermined positions f2 at which the leg-circumference elastic members 61d are placed which serve as the fold positions. Then, the opposing faces of the exterior sheet 14 folded in the thickness direction are joined together using the end joined portions 52 and the side joined portions 53. Accordingly, the leg-circumference extension sections 60 are formed to extend outward in the lateral direction. As described above, since no lateral welded regions 62 or vertical welded regions 66 are formed at the predetermined positions f2, the stiffness of the exterior sheet 14 does not become too high at the predetermined positions f2, thereby being able to tightly fold the exterior sheet 14. Thus, it is possible to form the leg-circumference extension sections 60 into neat planar shapes.

Then, the exterior sheet 14 is folded back on itself at the predetermined positions f2 such that the first lateral welded regions 63 and the first vertical welded regions 67 are superimposed in the thickness direction onto the second lateral welded regions 64 and the second vertical welded regions 68, thereby bringing about a state in which the leg-circumference elastic members 61b and 61c are sandwiched therebetween. That is, the leg-circumference extension sections 60 are formed such that at least a portion of the plurality of leg-circumference elastic members 61 overlaps with the lateral welded regions 62.

In such a diaper in which leg-circumference extension sections extend in the lateral direction to a large extent as in the diaper 1 (see FIG. 1), there has been a tendency to degrade the fit since the leg-circumference extension sections contract and/or curl in the lateral direction while the diaper is worn. In contrast thereto, in the diaper 1 manufactured by the manufacturing method according to an embodiment of the present disclosure, the lateral stiffness of the leg-circumference extension sections 60 is increased by providing the plurality of the lateral welded regions 62. This can make it easier to maintain the leg-circumference extension sections 60 in a planar shape. That is, even in a state in which a contraction force caused by the leg-circumference elastic members 61 is acting, it is possible to suppress contraction and curling of the leg-circumference extension sections 60 in the lateral direction, so that the leg-circumference extension sections 60 is likely to be maintained in a state of having some lateral width (wide-width state). Moreover, with a contraction force in the vertical direction acting while the leg-circumference extension sections 60 being maintained in the planar shape, many creases running along the lateral direction are formed in the surface of the leg-circumference extension sections 60. Such undulations of the creases can make it possible to achieve pleasant feel to the touch in the leg-circumference extension sections 60. This can make it possible to closely fit around the wearer's legs through contact of faces having wide widths thereby suppressing leakage of excrement from around the legs, while improving the fit of the leg-circumference extension sections 60 when the diaper 1 is worn.

Note that, as illustrated in the cross-section of FIG. 16, the diaper 1 has such a configuration that the exterior sheet 14 is folded back at the predetermined positions f2 and superimposed on itself in the thickness direction, and the back sheet 13 is interposed in the thickness direction between the leg-circumference elastic members 61a to 61c, and the end joined portions 52 and the side joined portions 53 in such a superimposed state. That is, in the absorbent main body 10, the leg-circumference elastic members 61a to 61c do not contact the end joined portions 52 and the side joined portions 53 in the thickness direction. If they are placed such that the end joined portions 52 and the side joined portions 53 are superimposed on the leg-circumference elastic members 61 in the thickness direction, the stretching force caused by the leg-circumference elastic members 61 acts also on portions other than a region L61 where the adhesive is applied to its surface in the leg-circumference elastic members 61. The two end portions in the vertical direction of the absorbent main body 10, and furthermore the front waist-circumference section 20 and the back waist-circumference section 30 might contract in the vertical direction. In contrast thereto, in an embodiment of the present disclosure, since the back sheet 13 is placed on the skin side of the leg-circumference elastic members 61, the end joined portions 52 and the side joined portions 53 are suppressed from contacting the leg-circumference elastic members 61, thereby suppressing the contraction force caused by the leg-circumference elastic members 61 from acting onto the front waist-circumference section 20, the back waist-circumference section 30, and the like.

In a state in which each of the leg-circumference extension sections 60 have been formed, the leg-circumference elastic member 61a located at the position innermost in the lateral direction among four leg-circumference elastic members 61a to 61d is placed at the position between the absorbent body 12 and the welded regions 62, 66 in the lateral direction. Thus, by virtue of the contraction of the leg-circumference elastic member 61a, a portion outside in the lateral direction of the leg-circumference elastic member 61a in the leg-circumference extension section 60 serves as the base for being raised to the skin side of the wearer when the diaper 1 is worn, and the upright height of the leg-circumference extension section 60 is ensured. Accordingly, the leg-circumference extension sections 60 are likely to closely fit around the legs of the wearer.

On the other hand, the leg-circumference elastic member 61d located at the position outermost in the lateral direction among four leg-circumference elastic members 61a to 61d is placed at the position corresponding to the laterally outer end 60d of the leg-circumference extension section 60. Accordingly, the leg-circumference extension sections 60 can be made in securely close contact with the wearer up to the position corresponding to the laterally outer ends 60d by virtue of the contraction of the leg-circumference elastic members 61d. In particular, since the lateral welded regions 62 do not reach the laterally outer ends 60d of the leg-circumference extension sections 60 in the diaper 1, the leg-circumference extension sections 60 might be less likely to be maintained in a planar shape in the region corresponding to the outside ends 60d. However, the leg-circumference extension sections 60 closely fit around the legs of the wearer using the contraction force of the leg-circumference elastic members 61*d*, thereby being able to suppress degradation in fit of the leg-circumference extension sections 60.

Further, when the leg-circumference extension sections 60 are formed in the extension section forming process (S105), the exterior sheet between the end joined portions 52 in a pair in the vertical direction is raised to the skin side of the wearer based on the side joined portions 53 by virtue of the contraction of the LSG elastic members 51, thereby forming the leak prevention wall sections 50. The side joined portions 53 (i.e., the bases for raising the leak prevention wall sections 50) are formed so as not to overlap with the welded regions 62, 66 in the lateral direction (S103), and thus the stiffness in the regions where the side joined portions 53 are formed in the exterior sheet 14 is not increased. Accordingly, the exterior sheet 14 is likely to be naturally bent about the bases of the side joined portions 53, so that the leak prevention wall sections 50 are easily raised.

In the diaper 1, the leak prevention wall sections 50 and the leg-circumference extension sections 60 can be integrally formed by folding the exterior sheet 14 back on itself. That is, in the diaper 1, there is no seam in sheet member among the absorbent main body 10, the leak prevention wall sections 50, and the leg-circumference extension sections 60. This makes it possible to suppress leakage of excrement from seams in sheets around the legs of the wearer.

The above embodiments of the present disclosure are simply to facilitate understanding of the present disclosure and are not in any way to be construed as limiting the present disclosure. The present disclosure may variously be changed or altered without departing from its gist and encompass equivalents thereof.

For example, such a diaper (so-called two piece type of diaper) may be employed that is integrated such that an exterior sheet 14 connects a front waist-circumference section 20 and a back waist-circumference section 30 together. Moreover, the absorbent article according to the present disclosure is not limited to a pull-on disposable diaper, but may be a tape-type disposable diaper. In a case of such a tape-type disposable diaper or the like, an elastic member that is stretchable in the lateral direction may be provided to at least one of waist-circumference sections in a pair. Other applications include pull-on sanitary napkins and urine absorbing pads.

REFERENCE SIGNS LIST

1: diaper (absorbent article, pull-on absorbent article);
10: absorbent main body; 11: top sheet;
12: absorbent body; 121: absorbent core; 122: core-wrapping sheet;
13: back sheet (liquid impermeable sheet); 14: exterior sheet (continuous sheet);
141: exterior continuous sheet;
20: front waist-circumference section (waist-circumference section); 21 sheet; 21 sheet
22: waist-circumference elastic member (elastic member stretchable in a lateral direction);
30: back waist-circumference section (waist-circumference section); 31 sheet; 31 sheet; waist-circumference elastic member (elastic member stretchable in a lateral direction);
40: adhesive region; 41: non-joined region; 42 to 44: joined region;
50: leak prevention wall section; 51: elastic member (LSG elastic member);
52: end joined portion; 53: side joined portion; 55: LSG adhesion portions;
60: leg-circumference extension sections (extension section);
60*a*: leg opening forming portion (portion where an extension section forms a leg opening); 60*b*: overlap portion;
61: leg-circumference elastic members (elastic member stretchable in a vertical direction);
62: lateral welded regions (welded region);
63: first lateral welded region (first welded region)
64: second lateral welded regions (second welded region)
66: vertical welded region; 67: first vertical welded region;
68: second vertical welded region; 69: weld portion;
LH: leg opening; and BH: waist opening.

The invention claimed is:

1. An absorbent article having a vertical direction and a lateral direction, the absorbent article comprising:
an absorbent main body including an absorbent body, the absorbent main body having a longitudinal direction that conforms to the vertical direction; and
waist-circumference sections in a pair respectively located on one end side and another end side in the longitudinal direction of the absorbent main body, the waist-circumference sections including an elastic member stretchable in the lateral direction,
the absorbent main body including leg-circumference extension sections in a pair respectively extending outward on two lateral sides of the absorbent body, the leg-circumference extension sections each having an elastic member stretchable in the vertical direction placed therein,
the leg-circumference extension sections being formed extending laterally outward from a position on a non-skin side of the absorbent body using a continuous sheet that is continuous in the lateral direction,
a welded region having a predetermined length in the lateral direction being placed in a portion where each of the leg-circumference extension sections forms a leg opening,
the welded region including a first welded region and a second welded region, and
in the portion where each of the leg-circumference extension sections forms the leg opening, a portion of the continuous sheet where the first welded region is placed and a portion of the continuous sheet where the second welded region is placed being superimposed on each other by being folded in a thickness direction of the leg-circumference extension sections.

2. The absorbent article according to claim 1, wherein at least a portion of the first welded region and at least a portion of the second welded region are not superimposed on each other in plan view in the thickness direction.

3. The absorbent article according to claim 1, wherein the welded region is placed inside of an outer end in the lateral direction of each of the leg-circumference extension sections.

4. The absorbent article according to claim 1, wherein the continuous sheet is folded on itself in the portion where each of the leg-circumference extension sections forms the leg opening,
a liquid impermeable sheet is placed between the absorbent body and the continuous sheet and between portions of the folded continuous sheet, and
the liquid impermeable sheet is placed inside of an outer end in the lateral direction of each of the leg-circumference extension sections.

5. The absorbent article according to claim 1, wherein the elastic member that is stretchable in the vertical direction and placed in each of the leg-circumference extension sections intersects with the welded region.

6. The absorbent article according to claim 1, wherein the elastic member that is stretchable in the vertical direction and placed in each of the leg-circumference extension sections is placed at a position between the absorbent body and the welded region in the lateral direction.

7. The absorbent article according to claim 1, wherein the elastic member that is stretchable in the vertical direction and placed in each of the leg-circumference extension sections is placed at a position of an outer end in the lateral direction of each of the leg-circumference extension sections.

8. The absorbent article according to claim 1, wherein the absorbent main body includes leak prevention wall sections in a pair in two lateral side portions of the absorbent body, respectively, the leak prevention wall sections being raisable toward a wearer, and
the leak prevention wall sections are formed using the continuous sheet.

9. The absorbent article according to claim 1, wherein the leg-circumference extension sections in a pair are formed using the continuous sheet that is shared between the leg-circumference extension sections.

* * * * *